United States Patent
Olesen et al.

(10) Patent No.: US 9,915,813 B2
(45) Date of Patent: *Mar. 13, 2018

(54) SYSTEM AND METHOD FOR TIME-RELATED MICROSCOPY OF BIOLOGICAL ORGANISMS

(75) Inventors: Tom Olesen, Gørløse (DK); Martin Christian Valvik, Hillerød (DK); Niels Agersnap Larsen, Lyngby (DK)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 523 days.

This patent is subject to a terminal disclaimer.

(21) Appl. No.: 13/513,500

(22) PCT Filed: Dec. 1, 2010

(86) PCT No.: PCT/DK2010/050327
§ 371 (c)(1),
(2), (4) Date: Jun. 1, 2012

(87) PCT Pub. No.: WO2011/066837
PCT Pub. Date: Jun. 9, 2011

(65) Prior Publication Data
US 2012/0244519 A1    Sep. 27, 2012

Related U.S. Application Data

(60) Provisional application No. 61/316,565, filed on Mar. 23, 2010.

(30) Foreign Application Priority Data

Dec. 4, 2009  (DK) .................................. 2009 01281

(51) Int. Cl.
*G02B 21/00* (2006.01)
*C12Q 1/00* (2006.01)
(Continued)

(52) U.S. Cl.
CPC .......... *G02B 21/0004* (2013.01); *C12Q 1/18* (2013.01); *G02B 21/365* (2013.01)

(58) Field of Classification Search
CPC ..... G02B 21/0004; G02B 21/365; C12Q 1/18
See application file for complete search history.

(56) References Cited

U.S. PATENT DOCUMENTS 3,814,522 A    6/1974   Clark et al.
3,921,622 A    11/1975  Cole
(Continued)

FOREIGN PATENT DOCUMENTS

EP    2 031 428 A1    3/2009
JP    2007-322685 A   12/2007
(Continued)

OTHER PUBLICATIONS

International Search Report dated Feb. 28, 2011, issued in corresponding International Application No. PCT/DK2010/050327. (3 pages).
(Continued)

*Primary Examiner* — Nathan A Bowers

(57) ABSTRACT

The invention relates to a system and a method for determination of a value for at least one parameter describing microbial activity of individual biological organisms in a liquid sample. Images, wherein individual biological organisms may be identified, are combined to provide optical sectionings of the biological organisms and the optical sectionings are analyzed to determine the value for said at least one parameter describing microbial activity of said individual biological organisms in each sample container.

42 Claims, 23 Drawing Sheets

(51) Int. Cl.
*C12Q 1/18* (2006.01)
*G02B 21/36* (2006.01)

(56) References Cited

U.S. PATENT DOCUMENTS

| | | |
|---|---|---|
| 4,448,534 A | 5/1984 | Wertz et al. |
| 5,102,392 A | 4/1992 | Sakai et al. |
| 5,123,275 A | 6/1992 | Daoud et al. |
| 5,329,461 A | 7/1994 | Allen et al. |
| 5,488,567 A | 1/1996 | Allen et al. |
| 5,649,032 A | 7/1997 | Burt et al. |
| 5,672,887 A | 9/1997 | Shaw et al. |
| 5,672,888 A | 9/1997 | Nakamura |
| 5,939,709 A | 8/1999 | Ghislain et al. |
| 6,153,400 A | 11/2000 | Matsumura et al. |
| 6,160,908 A | 12/2000 | Hakozaki |
| 6,313,452 B1 | 11/2001 | Paragano et al. |
| 6,656,683 B1 | 12/2003 | Reuben et al. |
| 6,867,851 B2 | 3/2005 | Blumenfeld et al. |
| 6,869,570 B2 | 3/2005 | Wardlaw |
| 6,873,725 B2 | 3/2005 | Xu |
| 6,919,960 B2 | 7/2005 | Hansen et al. |
| 7,058,233 B2 | 6/2006 | Silber |
| 7,068,365 B2 | 6/2006 | Hansel et al. |
| 7,194,118 B1 | 3/2007 | Harris et al. |
| 7,372,626 B2 | 5/2008 | Villa |
| 7,576,307 B2 | 8/2009 | Yazdanfar et al. |
| 7,630,628 B2 | 12/2009 | Ogihara et al. |
| 7,634,128 B2 | 12/2009 | Snow et al. |
| 7,634,129 B2 | 12/2009 | Strom |
| 7,764,821 B2 | 7/2010 | Coumans et al. |
| 7,860,302 B2 | 12/2010 | Sato et al. |
| 7,949,161 B2 | 5/2011 | Kawanabe et al. |
| 2002/0154216 A1 | 10/2002 | Yahiro |
| 2002/0155487 A1 | 10/2002 | Greenberger |
| 2003/0059866 A1* | 3/2003 | Lewis et al. .................. 435/34 |
| 2003/0103277 A1 | 6/2003 | Mohwinkel |
| 2003/0138139 A1 | 7/2003 | Strom |
| 2003/0151735 A1 | 8/2003 | Blumenfeld et al. |
| 2004/0008867 A1 | 1/2004 | Fein |
| 2005/0068614 A1 | 3/2005 | Yoneyama et al. |
| 2005/0148085 A1 | 7/2005 | Larsen |
| 2005/0179899 A1 | 8/2005 | Palti-Wasserman et al. |
| 2005/0259437 A1 | 11/2005 | Klein et al. |
| 2006/0084125 A1 | 4/2006 | Laor |
| 2007/0009395 A1 | 1/2007 | Jiang |
| 2007/0122143 A1 | 5/2007 | Okamoto |
| 2008/0011060 A1 | 1/2008 | Lynnworth |
| 2008/0100703 A1 | 5/2008 | Yamada |
| 2008/0192128 A1 | 8/2008 | Kempe et al. |
| 2008/0246946 A1 | 10/2008 | Hansen et al. |
| 2009/0021260 A1 | 1/2009 | Stringer |
| 2009/0059362 A1 | 3/2009 | Jansen |
| 2009/0208370 A1* | 8/2009 | Suzuki et al. .................. 422/52 |
| 2009/0226061 A1* | 9/2009 | Maiya ........................ 382/128 |
| 2009/0231689 A1 | 9/2009 | Pittsyn et al. |
| 2009/0239250 A1* | 9/2009 | Klug et al. ..................... 435/29 |
| 2009/0295963 A1 | 12/2009 | Bamford et al. |
| 2010/0208263 A1 | 8/2010 | Stevens et al. |
| 2010/0314533 A1 | 12/2010 | Stallinga et al. |
| 2011/0261164 A1 | 10/2011 | Olesen |
| 2012/0327404 A1 | 12/2012 | Olesen |
| 2013/0023041 A1* | 1/2013 | Greenberger et al. ..... 435/288.3 |

FOREIGN PATENT DOCUMENTS

| | | |
|---|---|---|
| RU | 2232988 | 7/2004 |
| WO | 89/01796 A1 | 3/1989 |
| WO | 98/56441 A1 | 12/1998 |
| WO | 00/55357 A1 | 9/2000 |
| WO | 02/35474 A1 | 5/2002 |
| WO | 02/055137 A2 | 7/2002 |
| WO | 02/084256 A1 | 10/2002 |
| WO | 03/058211 A1 | 7/2003 |
| WO | 03/095995 A1 | 11/2003 |
| WO | 2006/013312 A1 | 2/2006 |
| WO | 2007/036305 A1 | 4/2007 |
| WO | 2008/010761 A1 | 1/2008 |
| WO | WO-2008068891 A1 * | 6/2008 |
| WO | 2008/134678 A1 | 11/2008 |

OTHER PUBLICATIONS

Decision on Grant issued in corresponding Russian Patent Application No. 2011127424/28(040583), dated Apr. 22, 2014, and translation thereof.

Extended European Search Report dated Aug. 1, 2014, issued by the European Patent Office in the corresponding European Application No. 10834246.0 (8 pages).

International Search Report (Form PCT/ISA/210) mailed in International Application No. PCT/DK2009/050321 A1 dated Jan. 14, 2010, 3 sheets, Nordic Patent Institute, Taastrup, DK.

Written Opinion of the International Search Authority (Form PCT/ISA/237) mailed in International Application No. PCT/DK2009/050321 dated Jan. 14, 2010, 6 pages, Nordic Patent Institute, Taastrup, DK.

International Search Report (Form PCT/ISA/210) mailed in International Application No. PCT/DK2011/050064 dated Mar. 23, 2011 by the Nordic Patent Institute, Taastrup, DK (4 pages).

* cited by examiner

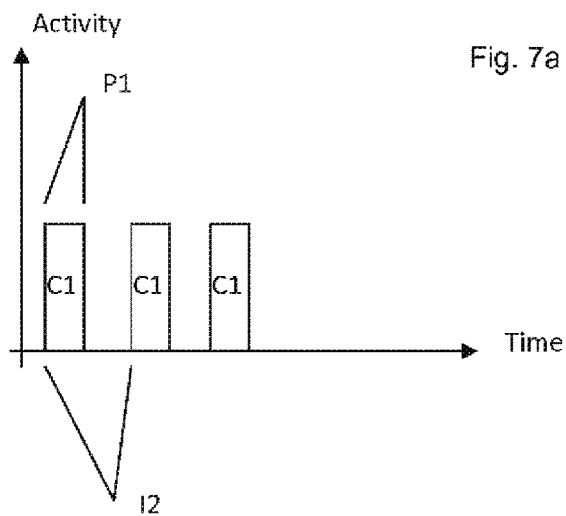
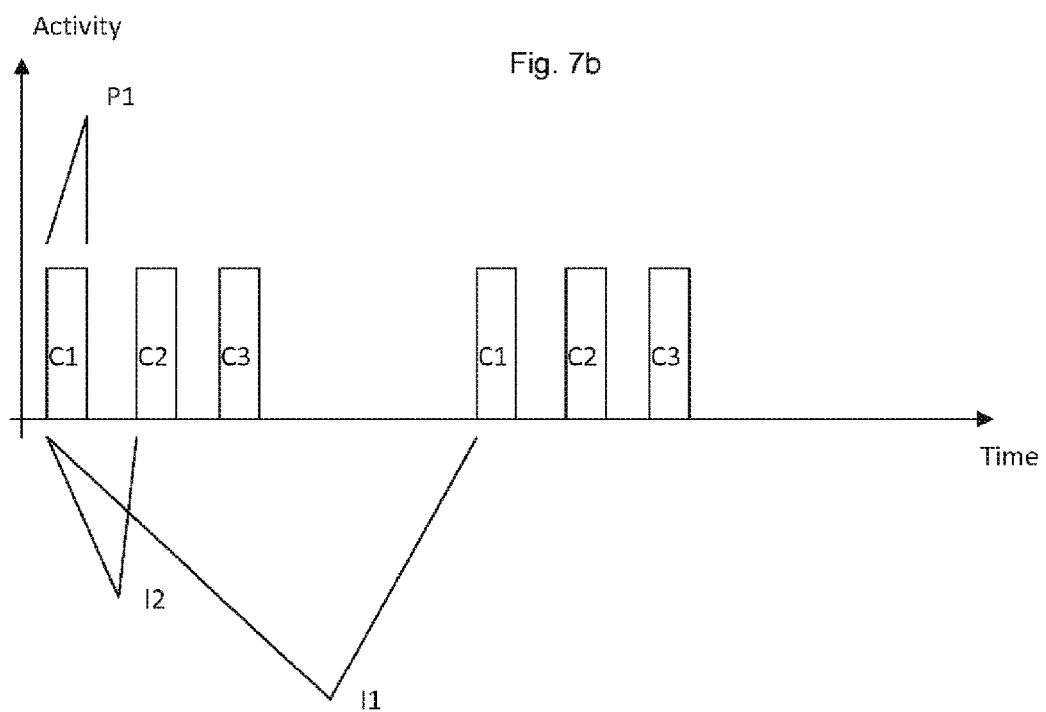

Fig. 16a    Fig. 16b    Fig. 16c
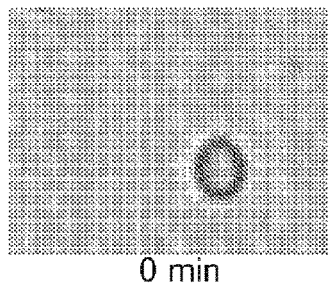 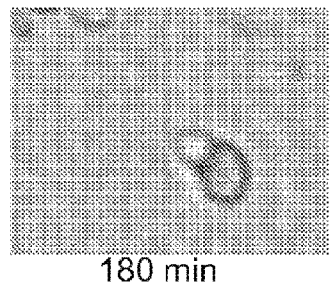 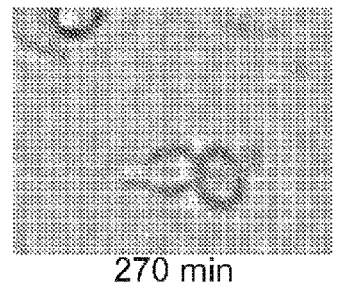
0 min    180 min    270 min
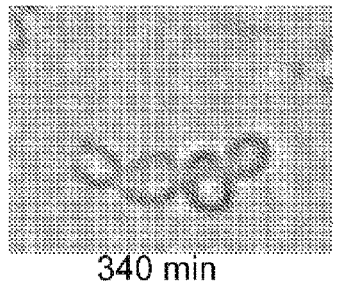 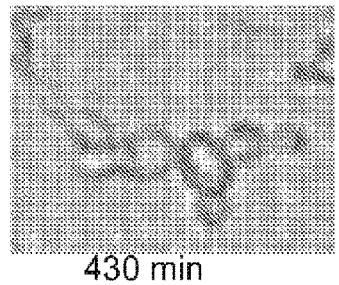 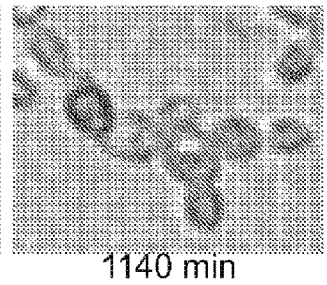
340 min    430 min    1140 min
Fig. 16d    Fig. 16e    Fig. 16f

SYSTEM AND METHOD FOR TIME-RELATED MICROSCOPY OF BIOLOGICAL ORGANISMS

BACKGROUND

Antibiotic susceptibility testing is a very important discipline used everywhere in hospitals, health clinics, medical production plants, food and drink production plants etc. The large number of different chemicals and standardized procedures and the enormous number of tests performed each year gives room for a huge industry benefitting of the micro organisms growing everywhere.

Some of the tests are indirect tests, i.e. measure or observe the presence of a derivate of microbial activity such as waste products or a redox indicator, instead of observing the microbial activity directly.

The costs of performing antibiotic susceptibility tests, e.g. in hospitals, are huge and growing continuously. Furthermore the long test incubation periods of up to 6 days pose a big problem, as treatments cannot await such long response times. The patient may be dead when the result is ready. Physicians thus often prescribe broad band antibiotics in order to start treatment immediately before results arrive. Faster results (within a few hours) may enable the use of narrow band antibiotics targeted directly at the cause of the disease, thereby minimizing the risk of creating resistance to antibiotics in general.

One of the most common susceptibility tests performed is testing urine for urinary tract infections (UTI). Urine is a very good growth medium in itself, and utmost care must be taken not to contaminate the urine with bacteria during urine sample handling. Furthermore it is necessary to start the testing in the laboratory within 1-2 hours if the reliability of the test results shall remain unaffected. In order to reduce the costs in health care systems, many small laboratories have been closed leaving only a few large laboratories often situated at hospitals. The urine sample must thus arrive at the central laboratory within 1-2 hours, which is not a problem at major hospitals, but when the sample is acquired at the GP the distance and transport time to the laboratory can be a problem. In these cases it may be necessary to refrigerate the urine samples and keep them in special containers until arrival at the laboratory. Even in hospitals where the laboratory may be in close proximity, it is beneficial to start a susceptibility testing immediately after sample acquisition, since this minimizes the test result delivery time. It is therefore desirable to have a small and easy-to-use apparatus for performing the susceptibility testing locally at the point of care.

Susceptibility testing of micro organisms comprises several levels of testing. One level may be to determine the types of micro organisms present in a sample, e.g. be bacteria, fungi, protozoa, algae or virus. Another level in the testing is to establish which type of antibiotic to be used for eliminating the micro organisms. The types of antibiotics may comprise narrow and broad spectre antibiotics as well as more specialised types. Similarly, tests may determine the best medication of the same type but from different producers.

Furthermore, it may be relevant to test the response of the micro organisms to different environments, such as aerobe and anaerobe, and in some cases even in phosphoric environments. Some situations may require testing the effect different levels and combinations of nutrition, especially when searching for specific types of micro organisms.

When the best antibiotic for destroying the micro organisms has been determined, it is important to determine the antibiotic concentration to be prescribed. Usually at least 5 different concentrations are tested, and up to 15 or more different concentrations may be used for determining the optimal concentration. The result of the concentration testing may be the MIT—Minimum Inhibitory Concentration, which indicates the concentration of the antibiotic necessary to prevent the micro organisms to grow. If concentrations below the MIT are used, the antibiotic will only eliminate some of the micro organisms, with the consequent risk of the remaining micro organisms to develop resistance or susceptibility toward the antibiotic.

Typically test results are formulated by categorizing the antibiotic candidates into Resistant, Intermediate or Susceptible.

Present test methods require the use of a large number of different chemicals and standardized procedures. The standards in US are maintained by CLSI (Clinical and Laboratory Standards Institute). The standards describe test details such as how to set up tests, including inoculation (concentrations), isolation distances, temperatures, inspection of growth results, incubation periods. Tests incubation periods may vary from a few hours (e.g. 16-24 hours) to several days (e.g. 3-6 days).

Often a 3 step method is used during incubation of the microorganisms. The first step is to incubate the primary culture. When a sufficiently high quality of the culture has been obtained, one or more monocultures are selected and isolated. The monocultures are then incubated again to obtain a sufficiently large amount of microorganisms for the last step—to incubate the microorganisms in Petri dishes or similar comprising different types and concentrations of antibiotics. The three steps is usually performed by hand and is thus expensive in manpower, and the time from the acquisition of the primary culture to the susceptibility testing may start is often many hours or several days.

The described complexity of susceptibility testing indicates the advantages of an apparatus that reduces the test time from many hours at the best to only few hours or even minutes. Furthermore, it would be advantageous to use more automated test procedures than is seen today, minimizing manual handling in laboratories. Finally, a cost reduction per test would obviously be of great benefit to all parts of the health care system.

Different solutions have been provided to overcome at least partly some of the problems described above.

One such solution is U.S. Pat. No. 6,153,400 Device and method for microbial antibiotic susceptibility testing by Matsumura et al. Matsumura provides a method and apparatus for performing microbial antibiotic susceptibility testing including disposable, multi-chambered susceptibility plates and an automated plate handler and image acquisition and processing instrument. The susceptibility plates are inoculated with a microorganism and anti-microbial agent(s) are applied such that the microorganism is exposed to a variety of concentrations, or a gradient of each anti-microbial agent. The plates are then placed in the instrument, which monitors and measures the growth of the microorganisms. This data is used to determine the susceptibility of the microorganism to the antibiotics. Such a system automates antimicrobial susceptibility testing using solid media and Kirby-Bauer standardized result reporting. The system is partly automatic, but handles agar disks for diffusion tests.

Another approach is shown in U.S. Pat. No. 4,448,534 Antibiotic susceptibility testing by Wertz et al. An apparatus is provided for automatically scanning electronically each well of a multi-well tray containing many liquid samples. A light source, preferably a single source, is passed through the wells to an array of photosensitive cells, one for each well. There is also a calibrating or comparison cell receiving the light. Electronic apparatus reads each cell in sequence, quickly completing the scan without physical movement of any parts. The resultant signals are compared with the signal from the comparison cell and with other signals or stored data and determinations are made and displayed or printed out. Thereby such matters as minimum inhibitory concentrations (MIC) of drugs and identification of microorganisms may be achieved. The apparatus according to U.S. Pat. No. 4,448,534 does not acquire an optical sectioning of said biological organisms.

Yet another system is filed as US patent application US 2005/0068614. A microscope system has a stage on which an observation sample including an observation object and a transparent member is to be placed, an objective lens which is placed to face the observation sample placed on the stage, a focusing unit which moves at least one of the stage and the objective lens to perform focusing operation, and an autofocus unit which controls a focusing driving unit by a so-called TTL system. After autofocus is performed for the transparent member by the autofocus unit, the focusing driving unit makes at least one of the stage and the objective lens move by a predetermined constant amount. The apparatus according to US patent application US 2005/0068614 does not acquire an optical sectioning of said biological organisms.

SUMMARY

It is an object of the present invention to provide a system and a method for performing microbial susceptibility testing that overcomes some of the aforementioned disadvantages and gives a fast, reliable and cost effective result compared to known systems and methods.

The method can be used directly on the clinical material, or on the clinical material after simple preparation, such as by dilution by a suitable substrate, mixing, centrifugation or filtration.

The system enables fast determination of bacterial antimicrobial resistance directly on the primary clinical sample material, without prior isolation of individual agents present in the clinical sample.

Thus the system is able to determine the optimal antimicrobial to be selected for treatment of an infection in just one incubation step, without the usual steps of incubating a primary culture, selecting colonies for monoculture and propagation and incubating again, applying resulting material to a conventional resistance test for yet another incubation.

In one embodiment, the system and method may be used for fast and reliable testing of a urine sample infected with bacteria for determination of the susceptibility to different antibiotics. It has been found that the system and method of the present invention is beneficial compared to other systems commonly used in health care institutions as it is faster and more cost effective, and at the same time reduces the need for manpower and manual handling of the samples.

In one embodiment of the present invention, the system and method may be used for investigation of different kinds of microscopic biological organisms by monitoring single specimens for a period of time in an environment similar to the natural habitat for the organisms. When monitoring microscopic biological organisms using traditional microscopes, the organisms must be placed on a microscope slide in a very thin layer. The thin layer leaves no room for the organisms to behave naturally, and it is usually not possible to control the environment in terms of nutrition, oxygen level, pH-value, etc. The present invention overcomes at least a part of these inconveniences.

Microscopic biological organisms may be present in clinical material such as faeces, swap samples from skin, lesions, serosal or mucosal surfaces, urine, lymph, pus, expectorate, transudate, exudate, glandular excretions such as milk, sweat, saliva, tear fluid, sebaceous discharge, nasal or other mucosal discharge, blood, cerebrospinal fluid, tumorous tissue, biopsies material from any tissue, extracelluar fluid, serum, plasma.

Thus, according to one embodiment of the present invention there is provided a system for determination of a value of at least one parameter describing microbial activity of individual biological organisms in a liquid sample. The system comprises an optical detection assembly comprising at least one image acquisition device adapted to acquire images wherein individual biological organisms may be identified. The system further comprises at least one sample device comprising at least one sample container for holding a sample in liquid form and at least one translating unit arranged to move the sample device and the optical detection assembly relative to each other. The system further comprises a control unit for controlling said optical detection assembly and said translating unit to acquire images to form at least a first optical sectioning of biological organisms in said liquid sample. An image analysing device is arranged to analyse said first optical sectioning, said image analysing device comprises algorithms adapted to determine said value for said at least one parameter describing microbial activity of said individual biological organisms in each sample container.

In one embodiment the control unit is adapted to sequentially acquire optical sectionings from said sample, such as said first optical sectioning and at least a second optical sectioning.

One object of the present invention is provided by a method for microbial activity in a liquid sample. The method comprises sequentially acquiring a plurality of optical sectionings of said liquid sample and selecting a first and a second optical sectioning from said plurality of sectionings. A value of at least one parameter for each optical sectioning is computed and it is determined if a change in the value of the at least one parameter has occurred between the acquisition of the two optical sectionings. The method further comprises determining the microbial activity on the liquid sample from the changes in the value of the at least one parameter.

One object of the present invention is provided by a method for determining of microbial activity in a liquid sample, said method comprising acquiring at least one optical sectioning of said liquid sample and selecting a first optical sectioning from said at least one optical sectioning. The method further comprises computing a value of at least one parameter for said first optical sectioning and determining said microbial activity in said liquid sample from said value of said at least one parameter.

In the context of the present invention, a parameter may in principle be any measurable parameter, such as, but not limited to, the cell division rate, cell viability living/dead rate, Brownian movements, metabolic rate, morphology, growth factor, kinetics or focus behaviour. The parameter may be understood to be a single value, a combination of several values or even a combination of several parameters.

In the context of the present invention, the phrase "biological organisms" may refer both to a single biological organism and an ensample of biological organisms, such as small or large groups of biological organisms. The method and system according to the present invention may thus be used to determine a value of at least one parameter describing microbial activity of one biological organism in a liquid sample and to determine a value of at least one parameter describing microbial activity of a plurality of individual biological organisms in a liquid sample.

Microbial activity may be the understood to be the activity created by cell division, cell movements, metabolic induced changes to the environment, cell death etc. creating changes in the population of the microscopic organisms, changes in the size of single organisms or clusters of organisms, or changes in the position or movements of the organisms. Microbial activity may therefore be understood in a very broad context to every change detectable for a single microscopic organism or in small groups or in a population of microscopic organism.

The system of the present invention comprises an optical detection assembly. The optical detection assembly comprises at least one image acquisition device comprised of a CCD-camera or a CMOS camera. The optical detection assembly further may be comprised of lenses, prisms, irises, apertures and other common optical components used in microscopy. The optical detection assembly may be adapted to acquire images wherein individual biological organisms may be identified. One embodiment of an optical detection assembly is described in US provisional application U.S. 61/146,850, wherein an apparatus for obtaining a plurality of images of a sample arranged in relation to a sample device is provided. The apparatus comprises at least a first optical detection assembly comprising at least a first image acquisition device. The first optical detection assembly has an optical axis and an object plane. The object plane comprises an image acquisition area from which electromagnetic waves can be detected as an image by the first image acquisition device. The apparatus further comprises at least one translation unit arranged to move the sample device and the first optical detection assembly relative to each other, and a housing arranged to support said first optical detection assembly and said translation unit, wherein said first optical detection assembly and said translation unit are arranged so that at least a part of said sample device is intersected by said image acquisition area. The movement of the sample device and the first optical detection assembly relative to each other is along a scanning path, which defines an angle theta relative to the optical axis, wherein theta is larger than zero. U.S. 61/146,850 also disclose a method for obtaining a plurality of images of a sample. This method comprises arranging said sample in relation to a sample device and arranging said sample device in relation to an apparatus for obtaining a plurality of images. The apparatus comprises at least a first optical detection assembly having at least a first image acquisition device. The first optical detection assembly is having an optical axis and an object plane, where the object plane has an image acquisition area from which electromagnetic waves can be detected as an image by the first image acquisition device. The image acquisition area intersects at least a part of said sample. The sample device and said first detection assembly are moved relative to each other over a scanning length along a first scanning path. The scanning path and the optical axis together define an angle theta, which is larger than zero. The method furthermore comprises obtaining said plurality of images. In U.S. 61/146, 850, is further disclosed a system for obtaining a plurality of images of a sample. The system comprises a sample device and an apparatus having at least a first optical detection assembly comprising at least a first image acquisition device. The first optical detection assembly of the apparatus has an optical axis and an object plane. This object plane comprises an image acquisition area from which electromagnetic waves can be detected as an image by the first image acquisition device. The apparatus of this system further comprises at least one translation unit arranged to move the sample device and the first optical detection assembly relative to each other, and a housing arranged to support said first optical detection assembly and said translation unit, wherein said first optical detection assembly and said translation unit are arranged so that at least a part of said sample device is intersected by said image acquisition area. The movement of the sample device and the first optical detection assembly relative to each other is along a scanning path, which defines an angle theta relative to the optical axis, wherein theta is larger than zero. In principle, the scanning path of U.S. 61/146,850, may comprise any movement of the object plane and the sample relative to each other. In particular, the scanning path may comprise a substantially straight scanning line arranged along a scanning axis. The scanning path may also be defined by a substantially rotational movement, in which case theta is the angle between said optical axis and the local tangential of said rotational movement. In one embodiment, the scanning path is confined to a plane, such as a straight line, a circular movement, a spiral movement, or any other suitable path.

In one embodiment, the biological organisms are at stand still during image acquisition. In the context of the present application, the phrase "substantially at stand still" refers to a situation, wherein the movement of the organisms in an inhomogeneous liquid sample does not affect the determination of the parameters of the sample, such as the parameters of organisms in the sample. In one embodiment, substantially at stand still refers to the situation where the movement of the organisms in the period of time lapsed in between the acquisition of two adjacent images in a sequence of spatially displaced images should be substantially smaller than the distance between these two adjacent images, such as one tenth of the distance. In one embodiment, substantially at stand still refers to the situation where there is no mass flow of said liquid sample during the acquisition of at least a part of said images. In one embodiment for imaging cells and their content, the movement of the cell may be limited to an extent whereby sufficiently sharp images of the cell can be obtained so that details relating to e.g. the nuclei can be determined. In embodiments adapted for determining parameters relating to cells, the term "substantially at stand still" thus may mean that the movement of said cells during the acquisition of an image may be limited to the Depth of Field (DOF) or a fraction of DOF, such as one thousandth of the (DOF), such as one hundredth of the DOF, such as one tenth of the DOF, such as one fifth of the DOF, such as one third of the DOF. The DOF may be in the range 0.1 micrometer to 200 micrometers. The movement of the organisms in the liquid sample at stand still conditions may hence be less than 0.001 micrometer per second, such as less than 0.01 micrometer per second, such as less than 0.1 micrometer per second, such as less than 1 micrometer per second. The organism parameter may in this embodiment be the number and size of nuclei or the distance between the nuclei in a cell. In one embodiment where the details of the organisms are of less interest, such as for counting organisms, the limitation on the organism movement is such that the counting of the organisms is not influenced by the movement.

The movement of the organisms to be counted may hence be less than 1 millimeter per second, such as less than 100 micrometer per second, such as less than 10 micrometer per second, such as less than 1 micrometer per second, such as less than 0.1 micrometer per second.

The depth of field is here defined as the range of distances from the imaging optics within which the image of the objects is substantially unaffected by displacements from the focal plane. The focal plane is defined as the plane where the best resolution of the imaging is attained. The term substantially unaffected implies that the estimated parameters, which characterizes the object features, are essentially unaffected by the translation. In one embodiment, substantially unaffected means that the ratio between the FWHM (Full Width Half Max) of the intensity distribution of a point source at a given position within the Depth of Field to the FWHM of the intensity distribution of a point source in the focal plane is less than 5, such as less than 2, such at less than 1.5, such as less than 1.25, such as less than 1.1, such as less than 1.05.

The system of the present invention comprises at least one sample device comprising at least one sample container for holding a sample in liquid form. The sample device may be comprised of glass material and/or a plastic material. In one embodiment, the material is substantially transparent at the wavelength(s) of the electromagnetic radiation used for acquiring the optical sectionings. The sample device may be a one-time-use only disposable unit, although it may be comprised of a re-usable material like glass. The amount of liquid sample in a sample container may be in the range of 0.1 micro liters to 100 micro liters. The number of sample containers in a sample device may vary depending on the application. A sample device which only comprises one sample container may for instance be used in an embodiment for monitoring one single biological organism. A sample device comprising several sample containers, such as 20 containers, may be used for susceptibility testing. The number of sample containers $N_{cont}$ on said sample device may be equal to 2, 3, 4, 5, 6, 8, 9, 10, 12, 14, 15, 16, 18, 20, 21, 22, 24, 25, 26, 27, 28, 30, or be more than 30. In one embodiment, the $N_{cont}$ sample containers are arranged in one or more rows, such as with the same number of sample containers in each row. The sample container may comprise an inlet to be used by the liquid to enter the sample container, and it may comprise an outlet to be used for ventilating excessive liquid or air during inlet of a liquid. The outlet may also be used for taking out the sample if the sample device is to be reused with a new sample of liquid sample. The sample container may have an open confinement i.e. be open in at least one direction, in which case the container may be considered to be a well-type container, or the sample may have a substantially closed confinement i.e. be substantially closed in all directions, besides the optional inlet and outlet, in which case it may be considered to a cuvette-type container.

The sample may be in liquid form while the optical sectioning is acquired. In the context of the present invention, a sample is considered to be in liquid form if the sample may flow by gravitational forces into the sample container or be drawn into the sample container using capillary forces. The liquid sample may behave as a gel. In the context of the present invention, a gel is a solid, jelly-like material that can have properties ranging from soft and weak to hard and tough. Gels exhibit substantially no flow when in the steady-state. By weight, gels are mostly liquid, yet they behave like solids An optical sectioning of a sample in a sample container comprises at least one image. The optical sectioning may also comprise several images, such as 10 images or even more such as 25, 40, 60 or even more.

The system of the present invention comprises a translation unit for moving the sample device and the optical detection assembly relative to each other. This may be accomplished by arranging said sample device in relation to a support which then is moved relative to the rest of the system while holding the optical detection assembly still, or vice versa moving the optical detection assembly relative to the rest of the system while holding the support of the sample device still. Both sample device and image acquisition may be moved simultaneously relative to the rest of the system.

In one embodiment, wherein measurements are to be carried out in one sample container only, the translation unit may be controlled to move the sample device relative to the optical detection assembly in small steps only while acquiring the images to be used for optical sectioning. The size of the steps may be below about 1000 micrometers, such as below about 100 micrometers, such as below about 10 micrometers, such as below about 1 micrometer, such as below about 0.1 micrometers.

The small steps may be varied from step to step. The length of the steps may be determined to be equal to DOF or a fraction thereof, or it may be equal to k times DOF where k is larger than 1.0.

In another embodiment, wherein measurements are to be carried out in several sample containers in a sequence, the translation unit may be controlled to move the sample device relative to the optical detection assembly in large steps when moving from one container to the next in the sequence, while the steps are kept small when acquiring images for optical sectioning within a sample container.

In one embodiment of the invention, an image analysing device analyses images and optical sectionings acquired from the sample containers.

Given an optical sectioning of a sample, the relevant objects, be it cells, bacteria or other objects of interest, may be extracted for further analysis by applying a first algorithm comprising:

1. Applying a decision function on each pixel in the optical sectioning, classifying each pixel as either object or background. The decision function could for example be based on the local contrast around the pixel in question.
2. Combining the object pixels from each image of the optical sectioning to form individual object focus stacks. An object focus stack consists of one or more images of an object imaged in different focus planes. Care has to be taken when constructing the object focus stacks if the optical sectioning is acquired using an oblique optical system as described in US provisional application U.S. 61/146,850
3. For each object focus stack the point of optimal focus can be determined using a focus function, applied to each image in the object focus stack. In one embodiment, where the objects in question are amplitude objects, the variance of the pixel intensities may be used as a focus function. At the image of maximum variance the object is said to be in focus. This image may be extracted for further analysis.

In one embodiment of the invention the image analysing device comprise algorithms adapted to determine cell division rate. Given a set of optical sectionings of a sample at equidistant or non-equidistant time intervals, the cell division rate is calculated by extracting the relevant cells using the first algorithm. For each object extracted a parameter regarding the cell may be calculated. This could for example be the number of sub components, the object area, the object perimeter, the size of the binary skeleton etc. The mean value of the parameter value for all objects in the optical sectioning may be calculated. This is repeated for all optical sectionings of the sample in question. By observing how the mean values vary over time, a cell division rate may be established. Other statistical measures than the mean of the parameter values may also be considered, such as the median, the variance, or other higher order and/or nonlinear statistical measures.

In one embodiment the image analysing device comprise algorithms adapted to determine cell viability. Given a single optical sectioning of a sample the degree of cell viability may be established by first applying the above mentioned method in order to extract the relevant object focus stacks. For each object the viability may be calculated by considering parameters such as the focus function behaviour, the intensity profile of the object in focus, the overall contrast of the object, the response of some biological staining etc. Applying this for all detected objects in the stack, statistical measures such as the mean can be used to judge the overall viability of the cells in the sample.

In one embodiment the image analysing device comprise algorithms adapted to determine living/dead rate. Given a set of optical sectionings of a sample at equidistant or non-equidistant time intervals the living/dead rate is calculated by extracting the relevant cells using the first algorithm. For each object extracted a parameter regarding living/dead properties may be calculated. This could for example be the focus function behaviour, the intensity profile of the object in focus, the overall contrast of the object, the response of some biological staining etc. The mean value of the parameter value for all objects in the optical sectioning may be calculated. This is repeated for all optical sectionings of the sample in question. By observing how the mean values vary over time, a living/dead rate may be established. Other statistical measures than the mean of the parameter values may also be considered, such as the median, the variance, or other higher order and/or nonlinear statistical measures.

In one embodiment the image analysing device comprise algorithms adapted to determine Brownian movements, which is determined by calculating. Given a single optical sectioning of a sample, the degree of Brownian movements may be established by first applying the above mentioned method in order to extract the relevant object focus stacks. For each object focus stack the degree of movement may be calculated by considering the movement of the centroid of the object at different focus planes. Applying this for all detected objects in the stack, statistical measures can be used to judge whether the movement is Brownian, or if there for example is a desired flow direction of the objects in the sample.

In one embodiment the image analysing device comprise algorithms adapted to determine morphology parameters. Given a single optical sectioning of a sample the morphological parameters of the object in the sample may be established by first applying the above mentioned method in order to extract the relevant objects in focus. For each object in focus various morphological parameters may be determined e.g. the number of sub components, the form factor, the object perimeter, the circularity, the granularity, the circular variance etc. Applying this for all detected objects in the optical sectioning, statistical measures can be used to calculate the overall morphological parameters of the objects in the sample.

In one embodiment the image analysing device comprise algorithms adapted to determine morphology changes over time. Given a set of optical sectionings of a sample at equidistant or non-equidistant time intervals the cell division rate is calculated by extracting the relevant cells using said first algorithm. For each object extracted, a parameter regarding the cell may be calculated. This could for example be the number of sub components, the form factor, the object perimeter, the circularity, the granularity, the circular variance etc. The mean value of the parameter value for all objects in the optical sectioning may be calculated. This is repeated for all optical sectionings of the sample in question. By observing how the mean values vary over time, the morphological changes over time may be established. Other statistical measures than the mean of the parameter values may also be considered, such as the median, the variance, or other higher order and/or nonlinear statistical measures.

The system and method may be adapted to determine the growth factor of biological organisms. The growth factor may be determined in order to e.g. extract information about how growth of the biological organisms is influenced by growth conditions, such as the sample environment and/or the introduction of one or more agents that interact with the biological organisms. In one embodiment the image analysing device comprise algorithms adapted to determine growth factor. Given a set of optical sectionings of a sample at equidistant or non-equidistant time intervals, the cell division rate may be calculated by extracting the relevant cells using said first algorithm. For each object extracted a parameter regarding the cell may be calculated. This could for example be the number of sub components, the object area, the object perimeter, the size of the binary skeleton, the shape characteristics etc. The mean value of the parameter value for all objects in the optical sectioning may be calculated. This is repeated for all optical sectionings of the sample in question. By observing how the mean values vary over time, a growth curve may be established. Other statistical measures than the mean of the parameter values may also be considered, such as the median, the variance, or other higher order and/or nonlinear statistical measures.

In one embodiment the image analysing device comprise algorithms adapted to determine kinetics. Given a single optical sectioning of a sample the kinetics of the object in the sample may be established by first applying the above mentioned method in order to extract the relevant object focus stacks. For each object focus stack the degree of movement may be calculated tracking the movement of the centroid of the object at different focus planes. This may be done by applying simple 2D image correlation. Here after various kinetics parameters can be extracted, direction of movement, velocity etc. Applying this for all detected objects in the optical sectioning, statistical measures can be used to calculate the overall kinetic properties of the objects in the sample.

In one embodiment the image analysing device comprise algorithms adapted to determine focus behaviour. Given a single object image stack the focus behaviour can be analyzed by considering the focus function. Various measures may be determined, for example the modality of the focus curve can reveal optical properties such as if the object is an amplitude or phase object. Other measures such as the width of the focus curve may also be applied.

The system further comprises a control unit, such as a computing device such as a PC or similar. The control unit may be a special computing device comprising a processor, RAM, external connection devices such as USB connection devices. The control unit may be an external unit located outside e.g. the housing of a microscope constructed according to the present invention.

In one embodiment of the present invention the optical detection assembly further comprises an image illumination device. The illumination device may be comprised of a laser, a diode laser, a LED a light bulb, a white light source or a polarized light source, but also other light sources should be considered to be within the scope of the present invention. The image illuminating device may be controlled by the control unit to illuminate the sample container during image acquisition.

In one embodiment of the invention, an external stimulation is applied to the liquid sample. The system may comprise a stimulating device for providing stimulation to the liquid sample in the sample container. The stimulation may e.g. be providing an electromagnetic field to the sample, providing a magnetic or electric field to the sample, or it may be applying an acoustic wave to the sample. The microscopic biological organisms may in one embodiment be imaged during stimulation to determine specific behaviour of the organisms which may help identify the species and nature of the organisms. The stimulating device may be controlled by the control unit to stimulate the sample container during image acquisition, or it may stimulate the sample container for a longer period to induce a more permanent change in the behaviour of the organisms.

In one embodiment of the present invention, the system further comprises a liquid sample environment controlling device. The liquid sample environment controlling device may be adapted to control the physical environment of said biological organisms in said liquid sample, such as the temperature of said liquid sample. The liquid sample environment controlling device may also be adapted to control the chemical environment of said liquid sample, such as the pH value, the level of nutrition, the partial pressure of gasses such as oxygen, nitrogen, hydrogen and carbon dioxide, the salinity, the level of alkali metal ions such as $Li^+$, $Na^+$ and $Ka^+$, the level of alkaline earth metals, such as $Mg^{2+}$ and $Ca^{2+}$.

The invention can in principle be used to determine parameters in relation to the microbial activity of any biological organism. In one embodiment of the present system and method, the biological organisms are selected from the group of bacteria, archaea, yeast, fungi, pollen, viruses, leukocytes, such as granulocytes, monocytes, Erythrocytes, Thrombocytes, oocytes, sperm, zygote, or stem cells.

The biological organism may be comprised in clinical material selected from the group of faeces, swap samples from skin, lesions, serosal or mucosal surfaces, urine, lymph, pus, expectorate, transudate, exudate, glandular excretions such as milk, sweat, saliva, tear fluid, sebaceous discharge, nasal or other mucosal discharge, blood, cerebrospinal fluid, tumorous tissue, biopsies material from any tissue, extracellular fluid, serum, plasma.

In principle, the biological organism may be comprised in any kind of liquid sample such as milk, beer, carbonated beverages, fruit juices, liquids utilized in fermentation processes, oils, water samples, such as water drawn from various stages of treatment of municipal or industrial water and wastewater treatment facilities, bottled water, water drawn from the natural environment, such as lakes, rivers, or oceans, water from a laboratory setting or a production facility, The invention may also be utilized to distinguish biological organisms from non-biological particles, and to distinguish living biological organisms from dead biological organisms.

The microbial activity comprises the microbial susceptibility of said biological organisms towards an antibiotic agent.

In one embodiment of the present invention, at least one sample container is inoculated with at least a first agent. Inoculation may be done before said liquid sample is introduced into said sample container, or it may be added after introducing the liquid sample to the sample container, i.e. while said liquid sample is in said sample container. The agent may be an antibiotic agent intended for destroying the biological organisms in the container, or it may be a nutrition agent intended for aiding the growth of the biological organisms. The agent may further be a cleaning detergent designed for destroying the biological organisms.

In one embodiment at least a part of the sample containers are inoculated with $N_{agent}$ different agents, where $N_{agent}$ may be 2, 3, 4, 5, 6, 8, 10, 20, or more than 20. It will be understood by a skilled person, that the number of different agents may depend on the measurement task at hand. If e.g. the susceptibility of bacteria to different kinds of bacteria is to be determined, it may be necessary to test using a large number of agents. In some cases the number of possible bacteria may be limited, and the number of different agents may be limited accordingly. In one embodiment, said sample containers are divided in groups of sample containers, where the sample containers of each group are inoculated with the same agent and sample containers of different groups are inoculated with different agents, such as a first group of said sample containers being inoculated with said first agent, a second group of said sample containers being inoculated with a second agent, a third group of said sample containers being inoculated with a third agent, a fourth group of said sample containers being inoculated with a fourth agent.

A sample container may also be prepared to probe e.g. the susceptibility of one biological organism toward several agents, such as a combination of agents. In one embodiment at least one sample container is inoculated with several different agents.

In one embodiment, at least one sample container is substantially free of an agent. By substantially free is meant that the amount of agent present in the container should be smaller than the amount of agent necessary to create an influence on the organisms in the container.

In one embodiment a first agent is inoculated in different concentrations in at least two different sample containers. When determining Minimum Inhibitory Concentration (MIT), which indicates the concentration of the antibiotic necessary to prevent the micro organisms to grow, it is advantageous to use several different concentrations in different containers at the same time. This speeds up the measurements, and the measurements may be compared as they may have been acquired using the same conditions and environment. In some cases it may be preferred that at least 5 or 10 different concentrations of agents are used when determining MIT. I other cases a different number of different concentrations of agents is preferred, such as below 5 concentrations or above 10 concentrations.

In one embodiment of the system of the present invention the control unit is adapted to acquire optical sectionings from at least one sample container over a period of time. The optical sectioning comprises at least one image, and in many cases several images. For some applications and biological organisms, the period of time used to acquire the optical sectioning(s) may be relatively long such as several days or several hours. For other applications and biological organisms the period for acquiring optical sectionings may be considerable shorter. In one embodiment, said period of time is below about 144 hours, such as below about 72 hours, such as below about 48 hours, such as below about 36 hours, such as below about 24 hours, such as below about 18 hours, such as below about 12 hours, such as below about 8 hours, such as below about 5 hours, such as below about 4 hours, such as below about 3 hours, such as below about 2 hours, such as below about 1.5 hours, such as below about 1 hours, such as below about 2700 seconds, such as below about 1800 seconds, such as below about 900 seconds, such as below about 600 seconds, such as below about 480 seconds, such as below about 300 seconds, such as below about 120 seconds, about 60 seconds, such as below about 10 seconds, such as below about 5 seconds, such as below about 2 seconds, such as below about 1 second. It will be appreciated by a skilled person that the mentioned periods are given in way of example and that the period may be varied depending on the measurement to be performed, and the period may be changed during measurement depending on the value of the parameter determined during measurement, such as changed individually for the different sample containers.

The system and method according to the present invention may be used to determine the microbial activity of biological organisms located in a plurality of sample containers. In the system, the control unit may be adapted to sequentially acquire optical sectionings from at least two different sample containers. In one embodiment optical sectionings are acquired from at least two different sample containers with a first time interval between the acquisitions of following two optical sectionings. The first interval may be below about 1800 seconds, such as below 900 seconds, such as below 600 seconds, such as below 300 seconds, such as below 120 seconds, such as below 60 seconds, such as below 30 seconds, such as below 10 seconds, such as below 5 seconds such as below 2 seconds such as below 1 seconds such as below 0.5 seconds such as below 0.2 seconds such as below 0.1 seconds, such as below 0.01 seconds such as below 0.001 seconds.

The system and method according to the present invention may determine the microbial activity of one or more biological organisms located in sample containers from a plurality of optical sectionings. In the system, the control unit may be adapted to sequentially acquire the optical sectionings. In one embodiment, said optical sectionings are sequentially acquired from a sample container with a second interval in time between two subsequent optical sectionings from the sample container. The interval may vary depending on the measurement to be performed. The second time interval may be below about 3600 seconds, such as below 1800 seconds, such as below 900 seconds, such as below 600 seconds, such as below 300 seconds, such as below 120 seconds, such as below 60 seconds, such as below 30 seconds, such as below 10 seconds, such as below 5 seconds such as below 2 seconds such as below 1 seconds such as below 0.5 seconds such as below 0.2 seconds such as below 0.1 seconds, such as below 0.01 seconds such as below 0.001 seconds. If the microbial activity of the sample is high, it may be advantageous to use a short interval, while a low microbial activity may call for a longer interval without losing important information. The interval may be changed during measurement depending on the determined value of the parameter, such as changed individually for the different sample containers.

In one embodiment, the control unit is adapted to stop image acquisition when the value of the parameter satisfies a predetermined condition. The predetermined condition may be related to the determination of antibiotic susceptibility of said biological organisms or it may be related to the determination of the minimum inhibitory concentration (MIT).

BRIEF DESCRIPTION OF DRAWINGS

The invention will be explained more fully below in connection with one embodiment and with reference to the drawings in which:

FIG. 7 shows a diagram showing scanning intervals and periods, FIG. 16 shows a close-up of a single yeast cell followed for 1140 minutes for monitoring cell divisions.

DETAILED DESCRIPTION

Figure 1:
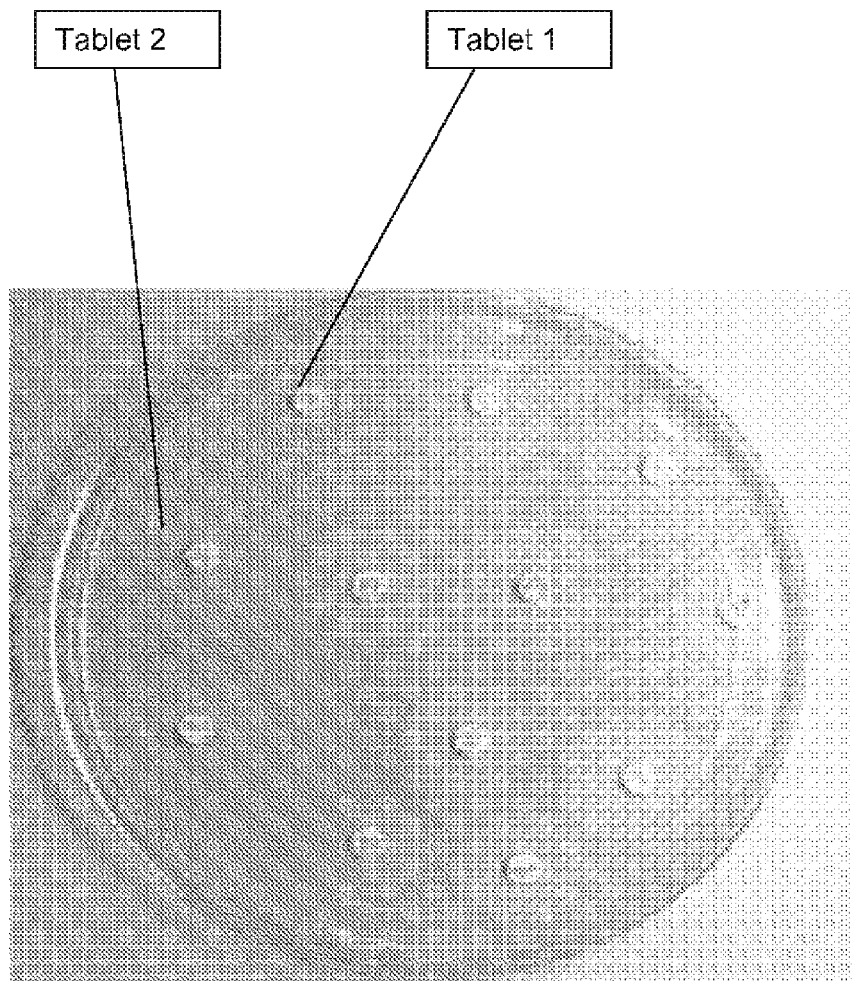
FIG. 1 shows an agar plate inoculated with a liquid comprising bacteria and tablets comprising antibiotics.

Further scope of applicability of the present invention will become apparent from the detailed description given hereinafter. However, it should be understood that the detailed description and specific examples, while indicating various embodiments of the invention, are given by way of illustration only, since various changes and modifications within the spirit and scope of the invention will become apparent to those skilled in the art from this detailed description.

The invention is defined by the features of the independent claim(s). Any reference numerals in the claims are intended to be non-limiting for their scope.

Some embodiments have been shown in the foregoing, but it should be stressed that the invention is not limited to these, but may be embodied in other ways within the subject-matter defined in the following claims.

In FIG. 1 a Petri dish comprising Agar is used for microbial antibiotic susceptibility testing. Bacteria have been added to the Agar on the plate, and 12 different tablets comprising different antibiotics have been evenly distributed on the plate. The plate is then incubated for a period, and the susceptibility may be determined by looking at the different sizes of the miscolouring around the tablets. The bacteria in the Petri dish are from the third step in the bacteria isolation process, where the first step has been to incubate the clinical material under test, the second step to isolate a single culture and incubate it, and the third step is the incubated single culture placed in one or more Petri dishes.

As may be seen the size of the miscoloured ring differs from very small at tablet no. 1, to very large at the tablet no. 2. The rest of the tablets used has miscoloured rings of different sizes between the sizes of Tablet No. 1 and tablet No. 2. It may therefore be determined, that antibiotic from the tablet no. 1 has very little effect on the bacteria in the agar substrate, while the antibiotic from the tablet no. 2 has the best effect on the bacteria. If the test result is to be used for prescribing medicine to a patient, the prescription would therefore be tablet no. 2. The incubation period was many hours, which was necessary for an accurate determination of the best antibiotic. If a shorter incubation period had been used, the difference in the sizes of the rings around the tablets would have been much smaller, making an accurate determination of the best antibiotic difficult.

Figure 2:
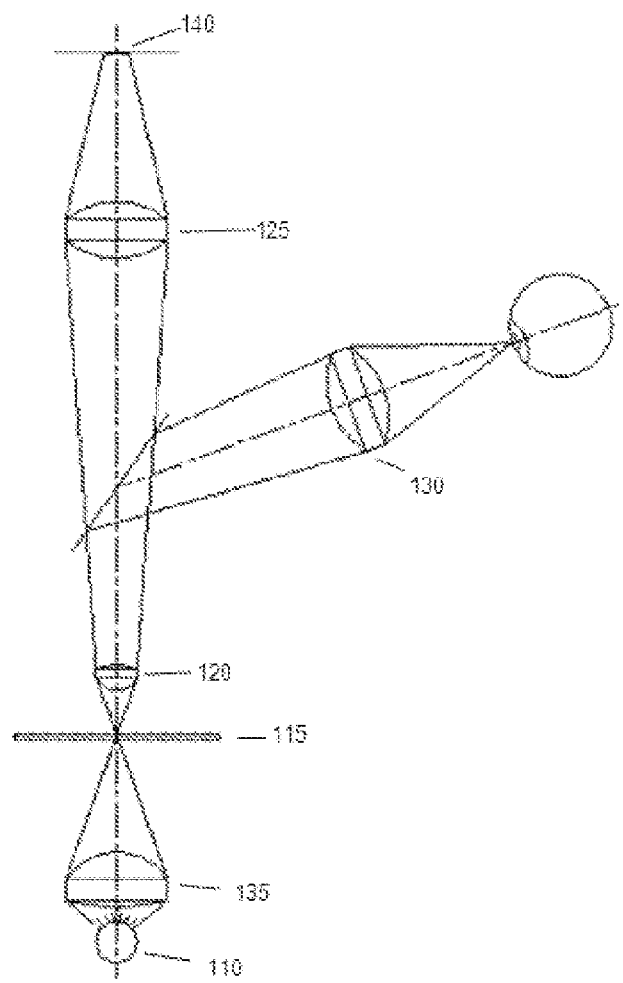
FIG. 2 shows a schematic side view of a standard optical microscope.

In FIG. 2 a schematic of a standard optical microscope is shown. The microscope comprises a holder 115 for holding a slide comprising a sample to be viewed. The microscope further comprises enlarging optics 120, illumination 110 and illumination optics 135, and an eyepiece 130. This particular optical microscope also comprises optics 125 for adding a camera 140 for capturing images of the substrate on the slide. In order to be able to view the microscopic particles the substrate to be viewed must be carefully prepared. The preparation may comprise adding a staining agent to stain the particles in the sample, and other method may also be applied such as filtering. When the sample is ready, it must be applied to the slide and a cover glass must be added. The cover glass ensures that the sample does not evaporate or run off of the slide, and it creates the very thin layer of sample necessary for the optical microscope to work properly. Using this optical microscope it is possible to view bacteria and other microscopic particles for determining the species and nature of them. Unfortunately it is not possible to follow the bacteria over a longer period of time in-situ or in an environment similar to their natural habitat. This is a major drawback in the study of the bacteria. It is e.g. not possible to view bacteria while adding an antibiotic to the sample—only the result at a specific time after the adding of antibiotic may be viewed. Even though the optical microscope gives some god images of bacteria, it is usually not used for microbial antibiotic susceptibility testing.

Figure 3:
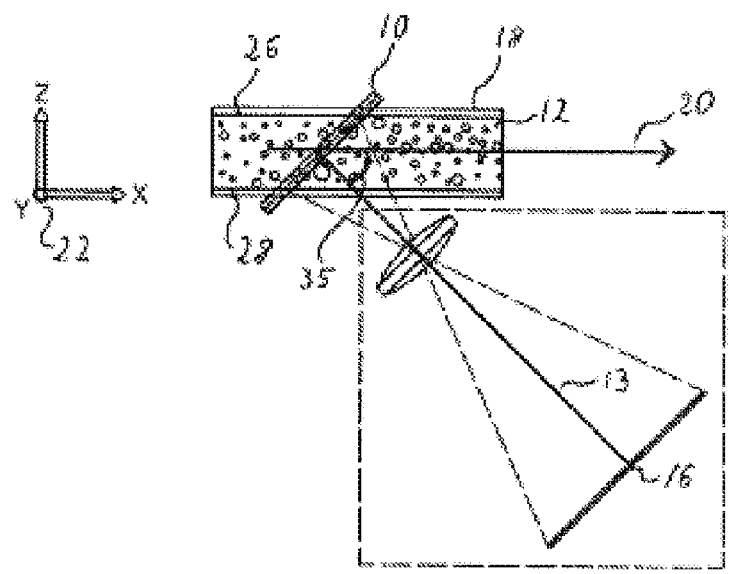
FIG. 3 shows a schematic side view of a measurement setup that may be used in one embodiment of the present invention.

In FIG. 3 a schematic view of an optical microscope suitable for making microbial antibiotic susceptibility testing is shown. The optical microscope is described in detail in provisional application no U.S. 61/146,850.

Figure 4:
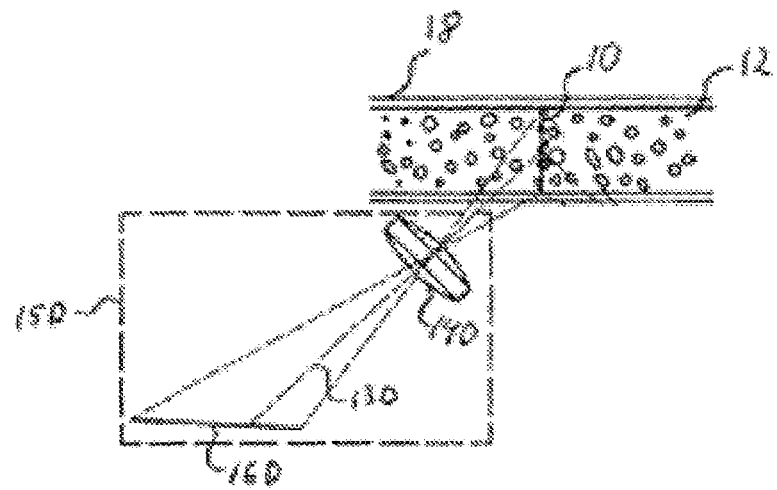
FIG. 4 is a schematic view of an optical scanning microscope where images are acquired vertically through the sample fluid.

The Scheimpflug principle is a geometric rule that describes the orientation of the plane of focus of an optical system when the lens plane is not parallel to the image plane. In FIG. 4 a schematic view of an optical microscope is shown, wherein the Scheimpflug principle has been applied during design of the microscope. A more detailed description of this optical setup may be found in provisional application no U.S. 61/146,850.

Figure 5:
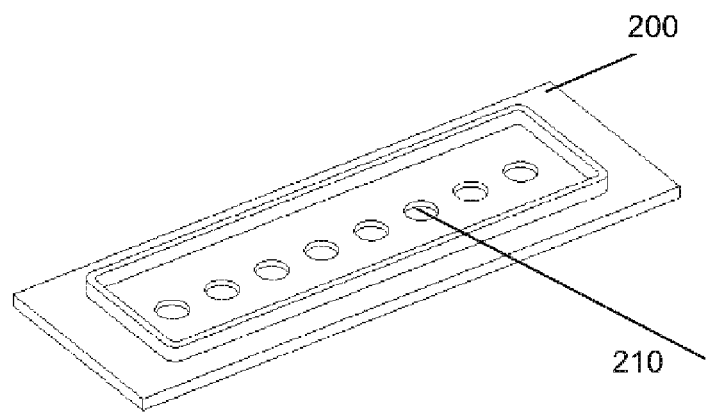
FIG. 5 shows one embodiment of a sample device comprising 8 sample containers.

In FIG. 5 an example of a sample device 200 comprising 8 sample containers 210 is shown. The sample containers 210 are of the open confinement type, wherein the sample may be added as droplets.

Figure 6:
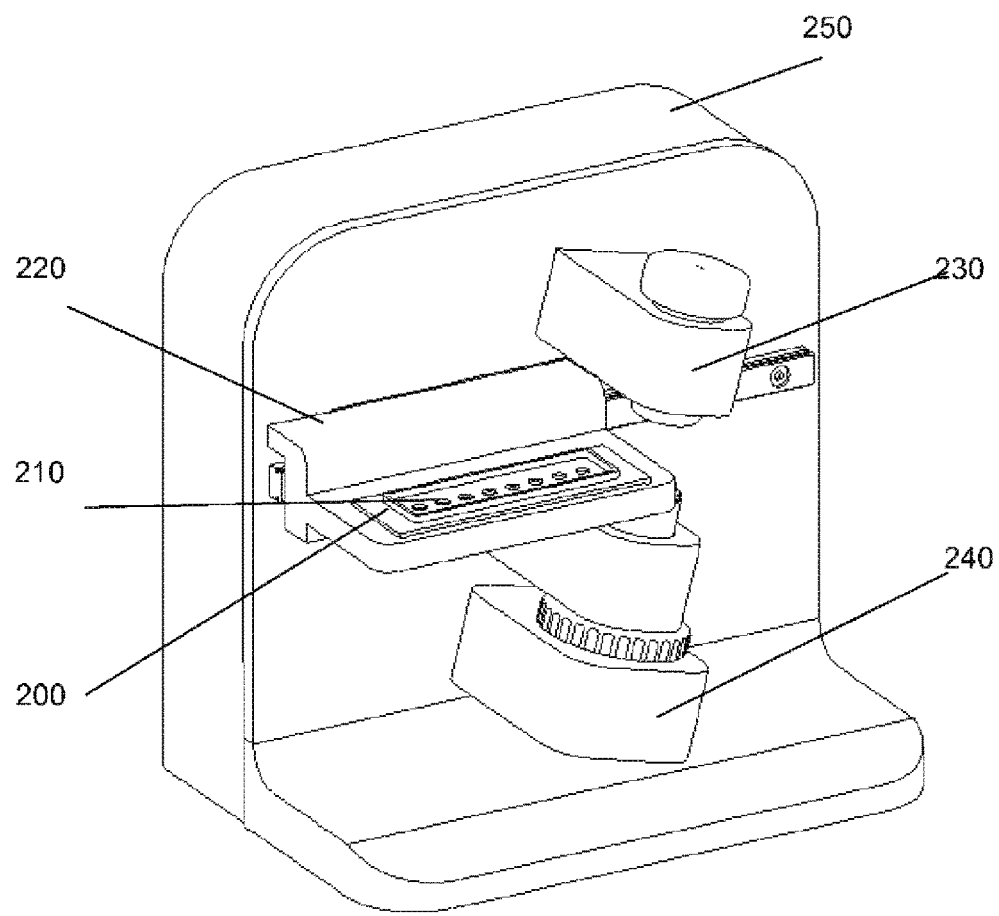
FIG. 6 shows a system comprising an optical microscope and a sample device.

In FIG. 6 an optical microscope 250 is shown comprising a sample holder 220 and a sample device 200 as shown in FIG. 6. The sample holder may be translated to position the sample containers 210 in relation to an optical imaging system 240 to acquire images of the sample. Illumination of the sample is made by illuminating device 230.

FIG. 7 is a diagram showing scanning intervals and periods. In FIG. 7a the sample container C1 is scanned in periods denoted P1 in intervals of I2. Each period is sufficiently long for acquiring at least one optical sectioning of the sample. The interval between each period may be very short—i.e. the optical sectioning is done in a substantially continuous manner, or it may be longer to reduce the amount of data acquired. In FIG. 7b the sample containers C1, C2 and C3 are scanned in periods denoted P1. Each period is sufficiently long for acquiring at least one optical sectioning of the sample. The interval between scanning of C1 and C2 and subsequent containers is denoted I2. I2 should be sufficiently long to let the translation device position the sample device in the correct position for scanning in the next container. The interval I1 denotes the interval between two subsequent scanning's of the same container Cn. The interval I1 should be sufficiently long to let the system scan all containers.

Figure 8:
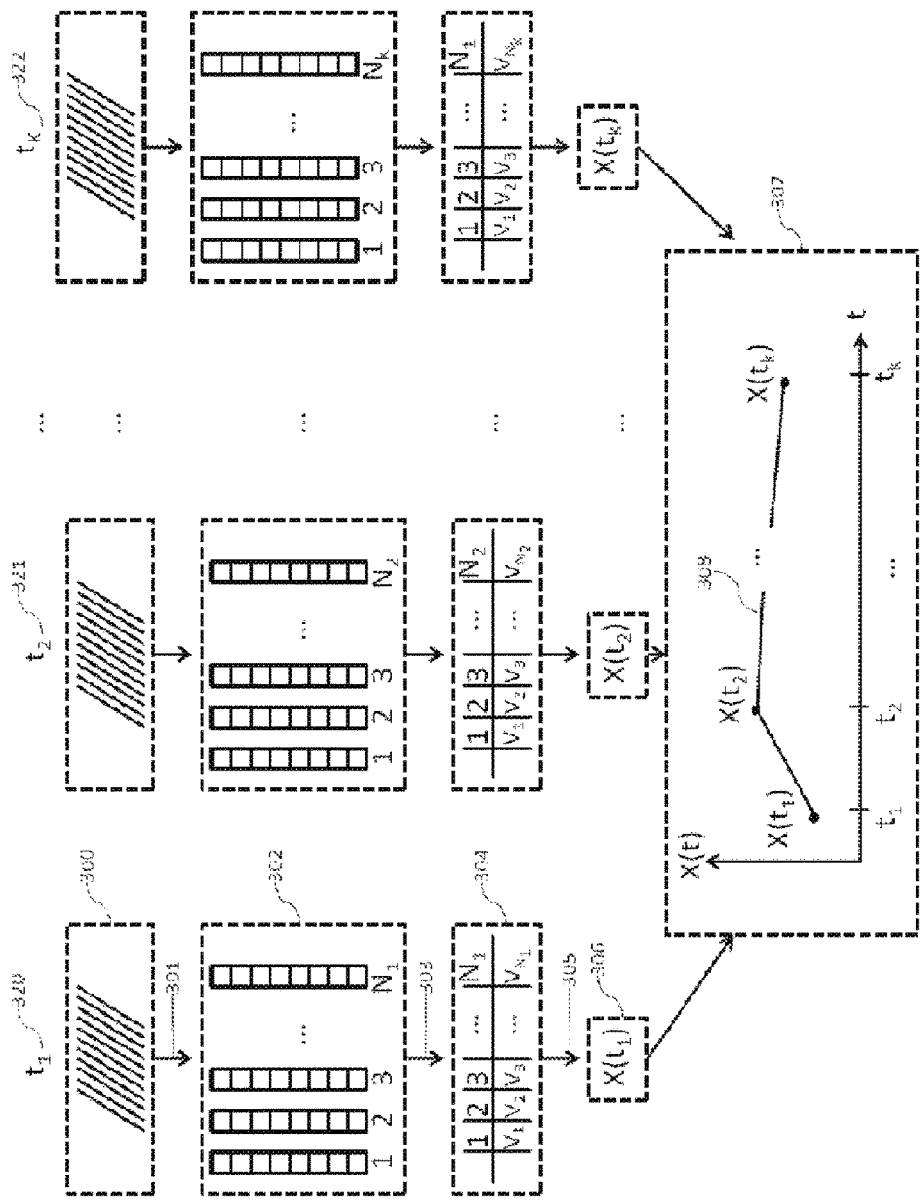
FIG. 8 shows a measurement process of a single sample at k distinct points in time.

FIG. 8 shows a measurement process of a single sample at k distinct points in time 320, 321 and 322. For a certain time $t_1$ 320 an optical sectioning of a sample is acquired 300. An algorithm 301 is applied to the optical sectioning, which outputs the object focus stacks for all $N_1$ objects contained in the optical sectioning 302. Each object focus stack is represented in the figure by a rectangle containing the objects images of the object focus stack. Another algorithm 303 is applied to the object focus stacks which outputs the value of some parameter for each object focus stack 304. Yet another algorithm 305 is applied to the parameter values 304 which output a single value 306 describing the objects in the optical sectioning at time $t_1$. This value is denoted $X(t_1)$ 306. This process is repeated for all k points in time, yielding a vector of values $X(t)$, $t=t_1, t_2, \ldots, t_k$ which is graphically depicted as a function of time 307. The points may be connected by a straight line 308 or any other linear or nonlinear interpolation methods.

Figure 9:
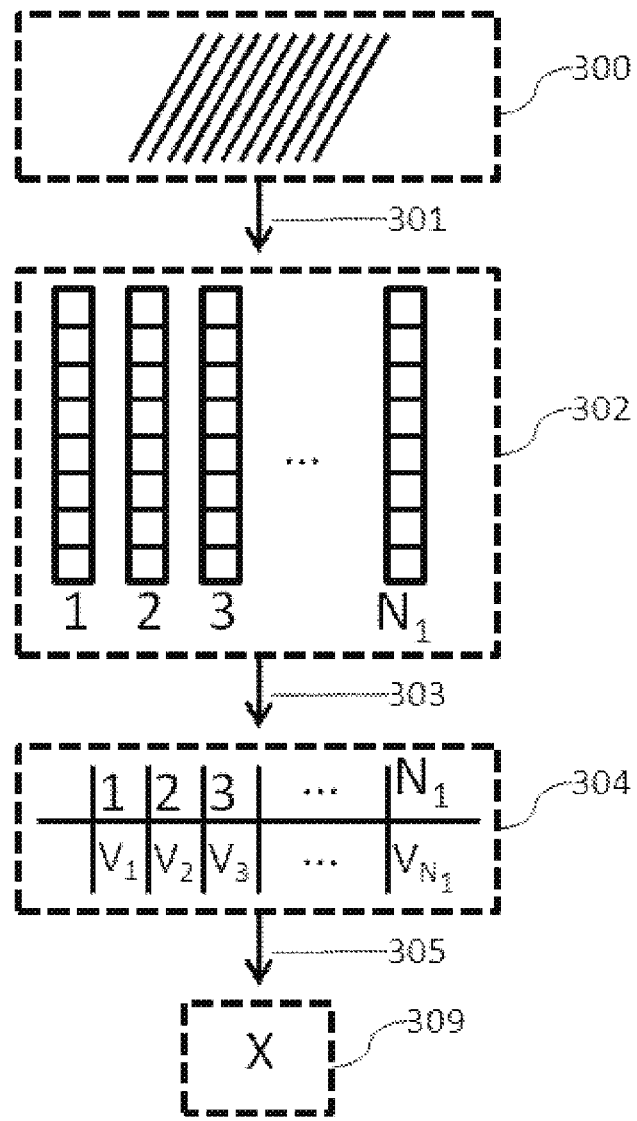
FIG. 9 shows a measurement process of a single sample at a single point in time.

FIG. 9 shows a measurement process of a single sample at a single point in time. An optical sectioning of the sample is acquired 300. An algorithm 301 is applied to the optical sectioning, which outputs the object focus stacks for all $N_1$ objects contained in the optical sectioning 302. Each object focus stack is represented in the figure by a rectangle containing the objects images of the object focus stack. Another algorithm 303 is applied to the object focus stacks which outputs the value of some parameter for each object focus stack 304. Yet another algorithm 305 is applied to the parameter values 304 which output a single value 309 describing the state of the objects in the sample. This could for example be the ratio between living and dead objects, the mean area etc.

Figure 10:
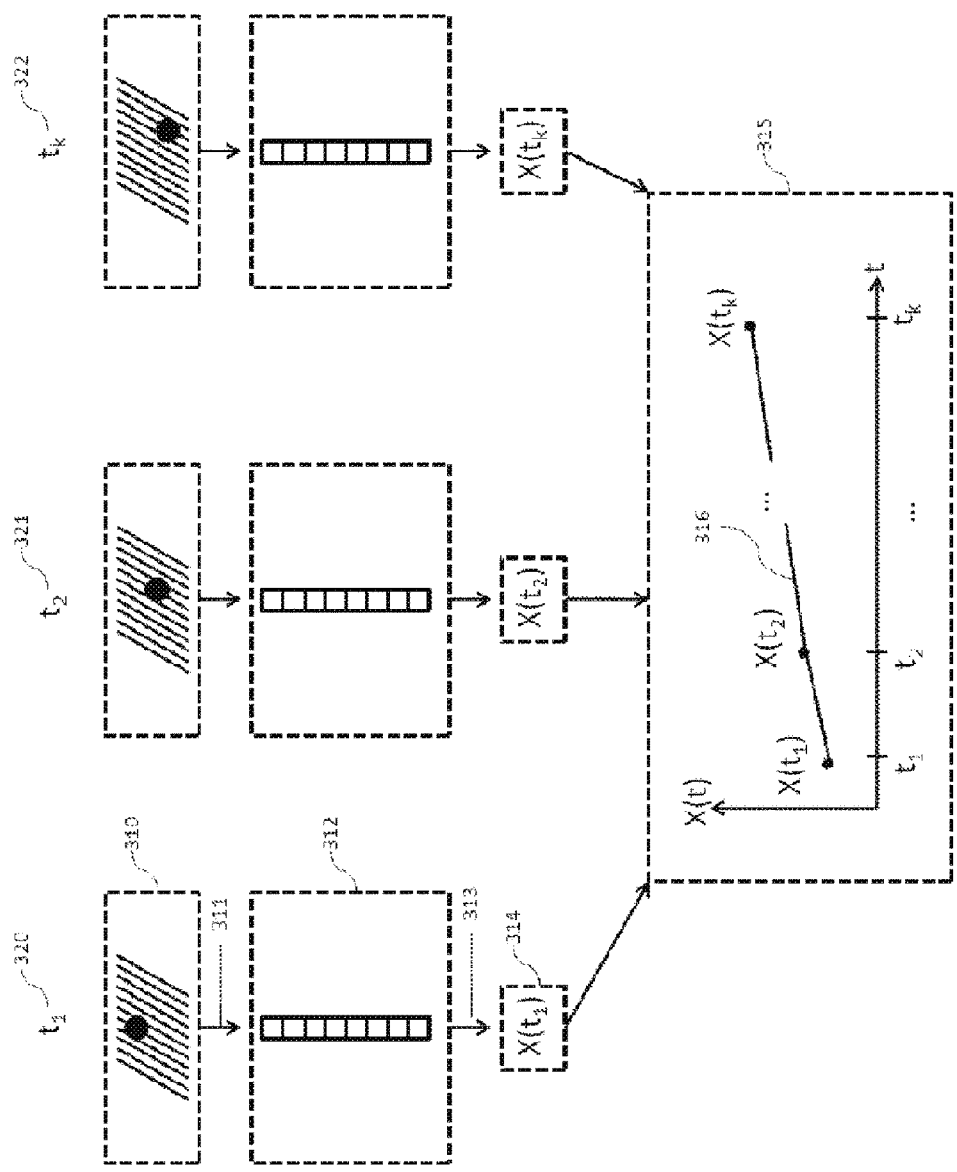
FIG. 10 shows a measurement process of a single sample where a single object is monitored.

FIG. 10 shows a measurement process of a single sample where a single object is monitored, at k distinct points in time 320, 321 and 322. For a certain time $t_1$ 320 an optical sectioning of a sample is acquired 310. An algorithm 311 is applied which identifies the object of interest, and extract its object focus stack 312. Another algorithm 313 is applied to the object focus stack 312 which calculates the value of some parameter describing the object. The value of the parameter is stored in $X(t_1)$ 314. This process is repeated for all k points in time, yielding a vector of values X(t), $t=t_1, t_2, \ldots, t_k$ which is graphically depicted as function of time 315. The points may be connected by a straight line 316 or any other linear or nonlinear interpolation methods.

Figure 11:
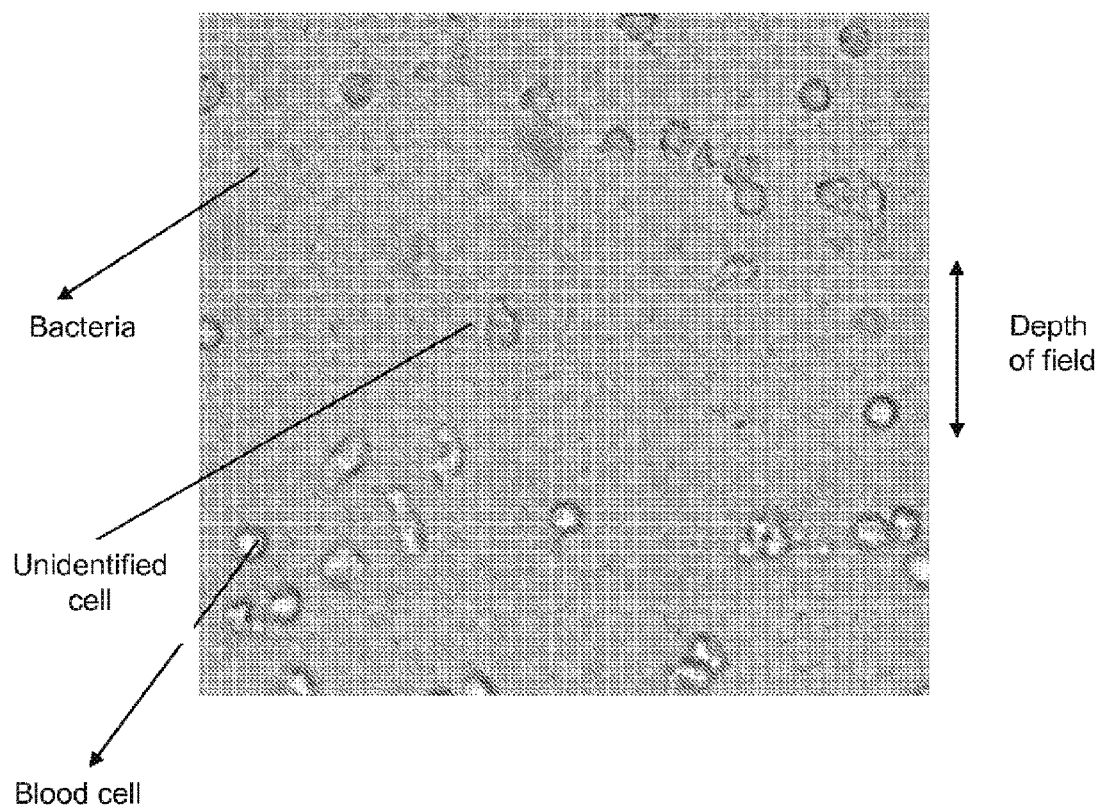
FIG. 11 shows an image of a first urine sample comprising bacteria, crystals and white blood cells.

In FIG. 11 an image of a first urine sample is shown, imaged using a bright field microscope. The sample comprises bacteria, red and white blood cells and other unidentified cells. This image and subsequent images are acquired using an optical setup similar to the one displayed in FIG. 3. Only approximately the middle quarter of the image may be considered to be within the depth of field of the optical system. In the image a large number of small black particles may be seen, which may be identified as bacteria. Furthermore some white blood cells may be seen, as well as a few objects which are difficult to identify. Normal urine comprises some waste products from the body, and some of these waste products may form crystal like objects.

Figure 12:
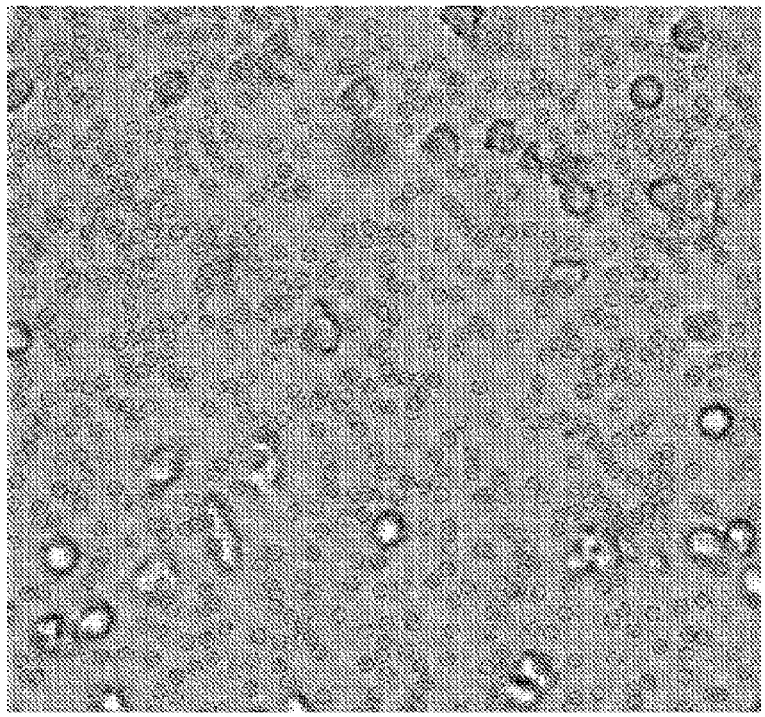
FIG. 12 shows the same image as in the previous image but with bacteria marked using a circle for each bacterium.

In FIG. 12 the same image as in FIG. 10 is shown, but with bacteria marked using a circle for each bacterium. The bacteria are identified using algorithms comprising a detection step where each pixel in the image is classified as either bacteria or background using a decision function based on a local contrast measure, and an identification step where connected bacteria pixels are grouped into connected components of pixels, each component representing a single bacterium. Hereafter the bacteria may be counted, or further analyzed.

Figure 13:
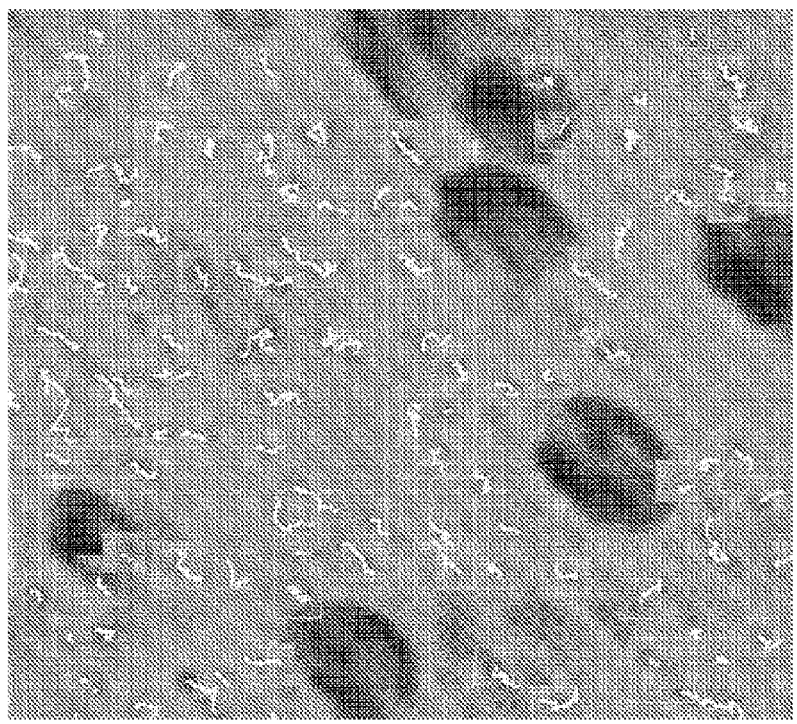
FIG. 13 shows an image of a second urine sample comprising bacteria, wherein the bacteria are monitored for app. 20 sec.

In FIG. 13 an image of a second urine sample is shown. The sample is comprised of pathological urine and comprises bacteria and some large objects which comprise epithelial cells. The depicted image is a projection of an optical sectioning of the urine sample. The optical sectioning of the sample comprises 20 images. The movement of the bacteria has been tracked for at period of 20 seconds, and the white trails show the path of each bacterium. The tracking is conducted by applying the same algorithm as described in FIG. 10 to each individual image of the optical sectioning. Between each image, objects are matched one-to-one in order to track the objects through the optical sectioning. The coordinates of each object are stored, and can be analyzed further. The motion path of this particular sample is seen to be a combination of Brownian motion (random movement) and a collective diagonal movement caused by a flow of the fluid. In this case all individual bacteria exhibit the same motion characteristics. In other samples containing multiple bacteria cultures, it may be possible to distinguish between active and inactive (dormant or dead) individuals. In this particular image only 2D information is used. Using information obtained during the optical sectioning regarding the 3D information about the motion path of the bacteria, a 3D tracking may be determined giving even more information regarding the single bacteria and enabling a differentiation of different species of bacteria.

Figure 14:
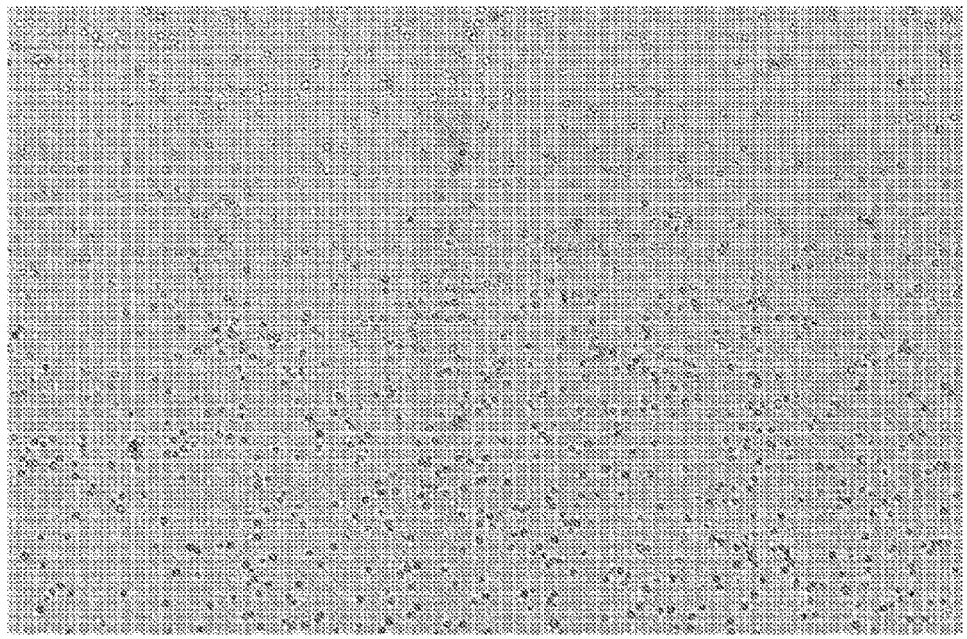
FIG. 14 shows an image of a fluid sample comprising baker's yeast

In FIG. 14 an image of yeast diluted in water and mixed with a nutrition agent is shown. Yeast is commonly used in fermentation and in this case baker's yeast has been used, as it is very easy to handle. The sample of yeast has been kept in temperatures around 22° C., and the nutrition agent was only sparsely added to avoid the yeast to grow too much. As in FIGS. 11 and 12 it is only approximately the middle quarter of the image that may be considered to be within the depth of field (DOF) of the optical system. In the image a large number of yeast cells may be seen. Some of the cells are positioned below the DOF, while others are positioned above the DOF. Although a majority of the cells are outside the DOF, they are imaged in a quality that may qualify them for counting, and they may be used in combination with other images of the same sample but with the DOF area slightly translated in order to make optical sectioning. It is also possible to use the image for object mobility and growth kinetics.

Figure 15:
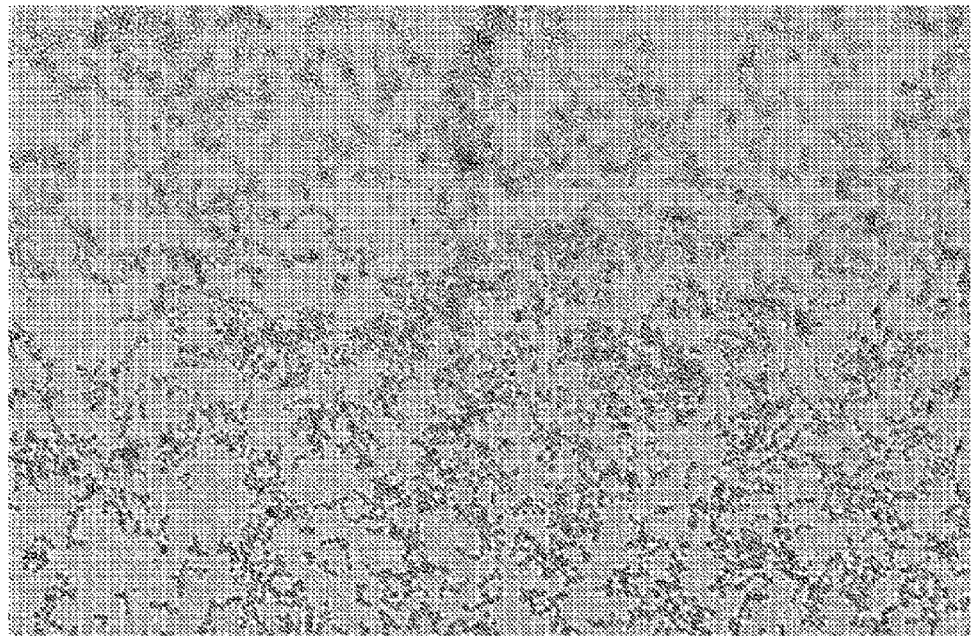
FIG. 15 shows an image of the same fluid sample as in FIG. 14 but after 19 hours.

In FIG. 15 the same sample comprising yeast is imaged after approximately 19 hours. Although the temperature was kept relatively low and the concentration of the nutrition agent was kept at a minimum, the number of yeast cells has greatly increased during the 19 hours.

In FIG. 16a a yeast cell has been singled out for monitoring. In FIG. 16b-16f the same yeast cell is shown at later stages. During the 19 hours app. 3 additional generations of yeast cells is generated from the first single cell forming a small cluster. A few other cells from neighbouring clusters may also be detected in the images.

Figure 17:
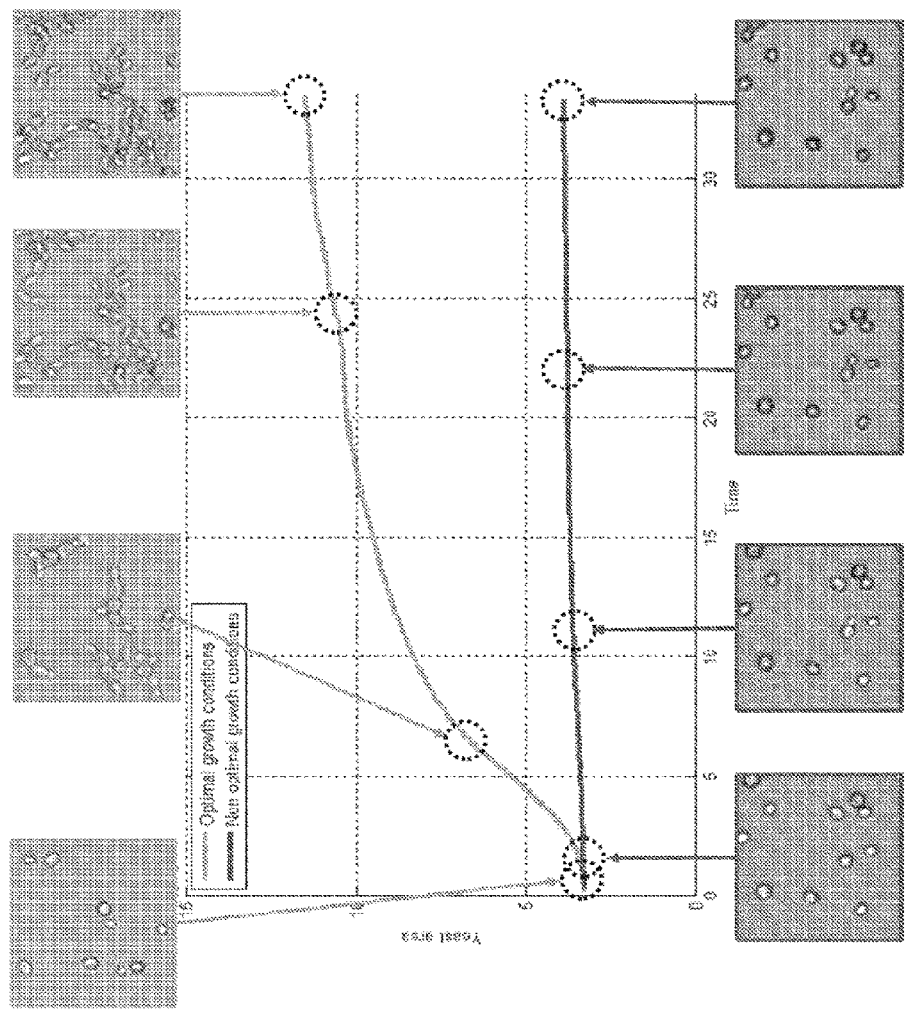
FIG. 17 shows two growth curves for yeast samples—one comprising a nutrition agent, and one without.

In FIG. 17 two growth curves are displayed. Both growth curves are determined using a sample comprising baker's yeast. The curves display the total area of the image comprising yeast cells. The lower curve displays a sample of yeast without adding a nutrition agent. It is seen that the number of yeast cells does not change and the yeast cells are not dividing to create clusters of new cells. The upper curve displays a sample of yeast similar to the yeast in the lower curve, but a nutrition agent has been added to the sample to make the yeast cells grow and divide to form clusters. At a very early stage, the two curves are clearly separated, and it would not be necessary to let the yeast grow for 19 hours to decide which of the environmental conditions is the most suitable for the yeast cells.

Figure 18:
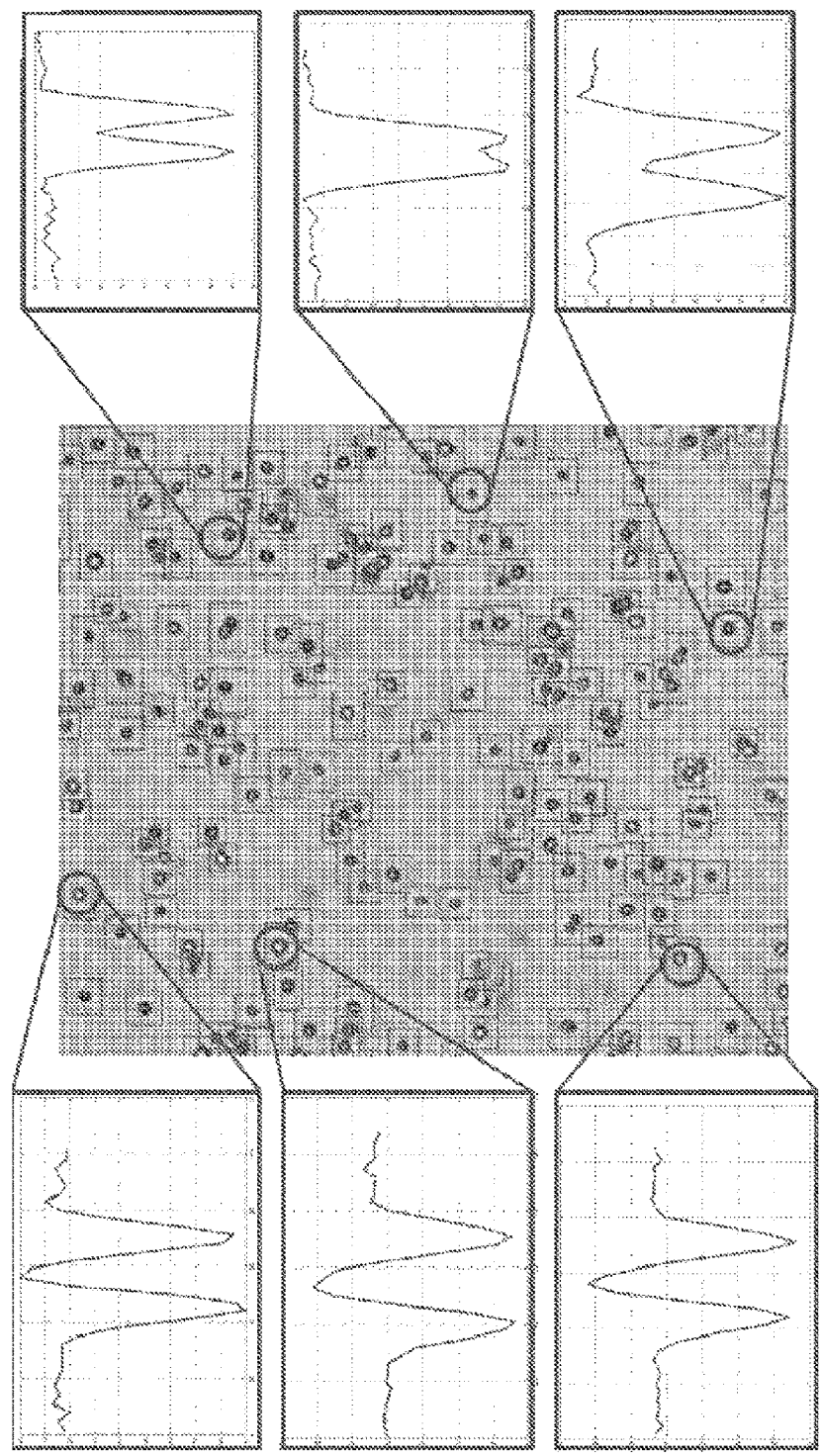
FIG. 18 shows the result from determining a parameter for differentiating between living and dead cells.

In FIG. 18 yet another image of yeast is shown. The sample comprises both living and dead yeast cells. The sample has been prepared by mixing two samples of yeast—one sample comprising living cells, and one sample wherein the yeast cells have been killed by rising the temperature of the sample to a level where all living cells are killed. The yeast cells have then been stained using Trypan blue, which is a well known method for differentiating between living and dead cells. Living cells does not allow the Trypan blue to pass through the cell membrane, while dead cells do not maintain this ability. As a result dead cells are stained and living cells are not stained.

The sample of the yeast cells has been sectioned optically and a projection of the optical sectioning has been provided by extracting the sections of the images where the cells are imaged in focus. This projection, commonly denoted Extended Depth Of Field image (EDOF), therefore comprise images of cells all imaged in focus. A study of the image reveals two different types of cells—one type has a bright centre surrounded with a dark circle, while the other type has a smaller and darker centre (compared to the first type) surrounded with a dark circle. In FIG. 18 three examples of each type has been selected, and the pixel intensity values along a line through the cells are shown for each selected cell. The three selected cells at the left side has a bright centre indicating that the cell has not been stained, while the three cells at the right side has a somewhat darker centre indicating that the cells has been stained. Comparing with other measurements of stained living and dead cells before the cells are mixed indeed reveals that the cells with the bright centre are living cells, while the cells with the dark centre are dead cells.

Figure 19:
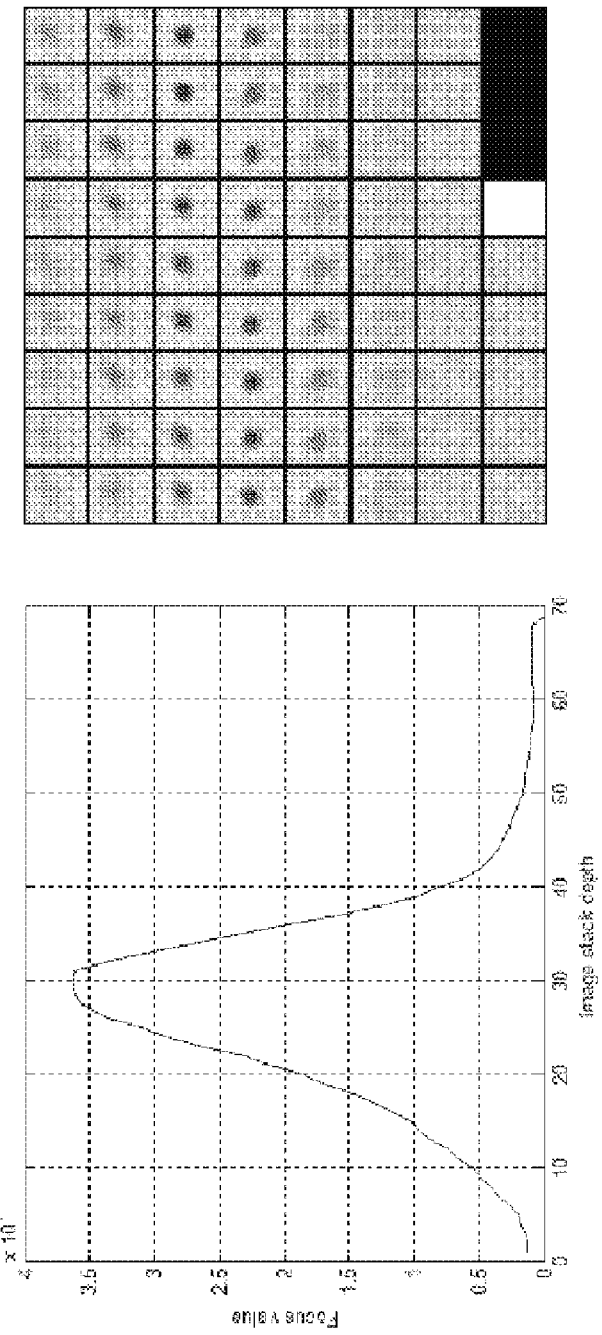
FIG. 19 shows an optical sectioning of a stained latex sphere.

In FIG. 19 an optical sectioning of a stained latex sphere is shown at the right. The optical sectioning comprises 68 different images of the latex sphere. The latex sphere is 5 µm in diameter. Such latex spheres are commonly used as calibration standards in the field of optical microscopy. For each image of the optical sectioning a focus function has been applied, yielding a focus value for each of the 68 images. In this case, the focus function is the variance of the pixel intensity values of the image. The focus values are shown graphically in the left part of the figure as a function of image number. A stained latex sphere is a true amplitude object—i.e. the amplitude of the light is attenuated depending on the thickness and density of the object. As may be seen, the focus value is getting higher the closer the latex sphere is imaged in focus. The shape of the focus function is clearly unimodal, i.e. it has one well defined maximum.

Figure 20:
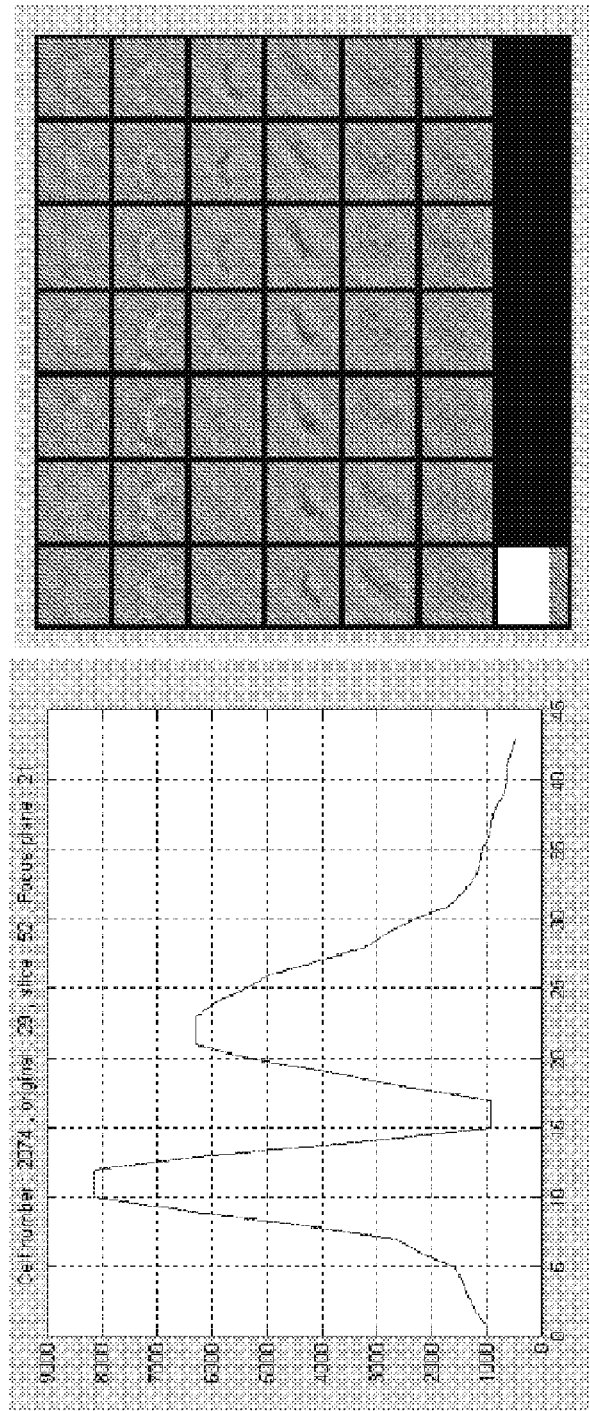
FIG. 20 shows an optical sectioning an *Acidophilus* bacterium

In FIG. 20 an optical sectioning of an unstained *Acidophilus* bacterium is shown at the right. The optical sectioning comprises 42 different images of the bacterium. The bacterium is a true phase object, i.e. it is not possible to see the bacterium in focus using a conventional bright field microscope. But if the microscope is positively or negatively defocused around the focus of the bacterium an image of the bacterium will appear. For each of the 42 images in the optical sectioning the focus value has been calculated and the values are displayed graphically as a function of image number at the right of FIG. 16. The graph is clearly bimodal, i.e. it has two well defined maxima—one for each side of the optimum focus position. This is a typical behaviour of a phase object. Under some circumstances it may be of importance to distinguish between phase objects and amplitude objects. By analyzing the shape of the focus curve this can be revealed.

Figure 21:
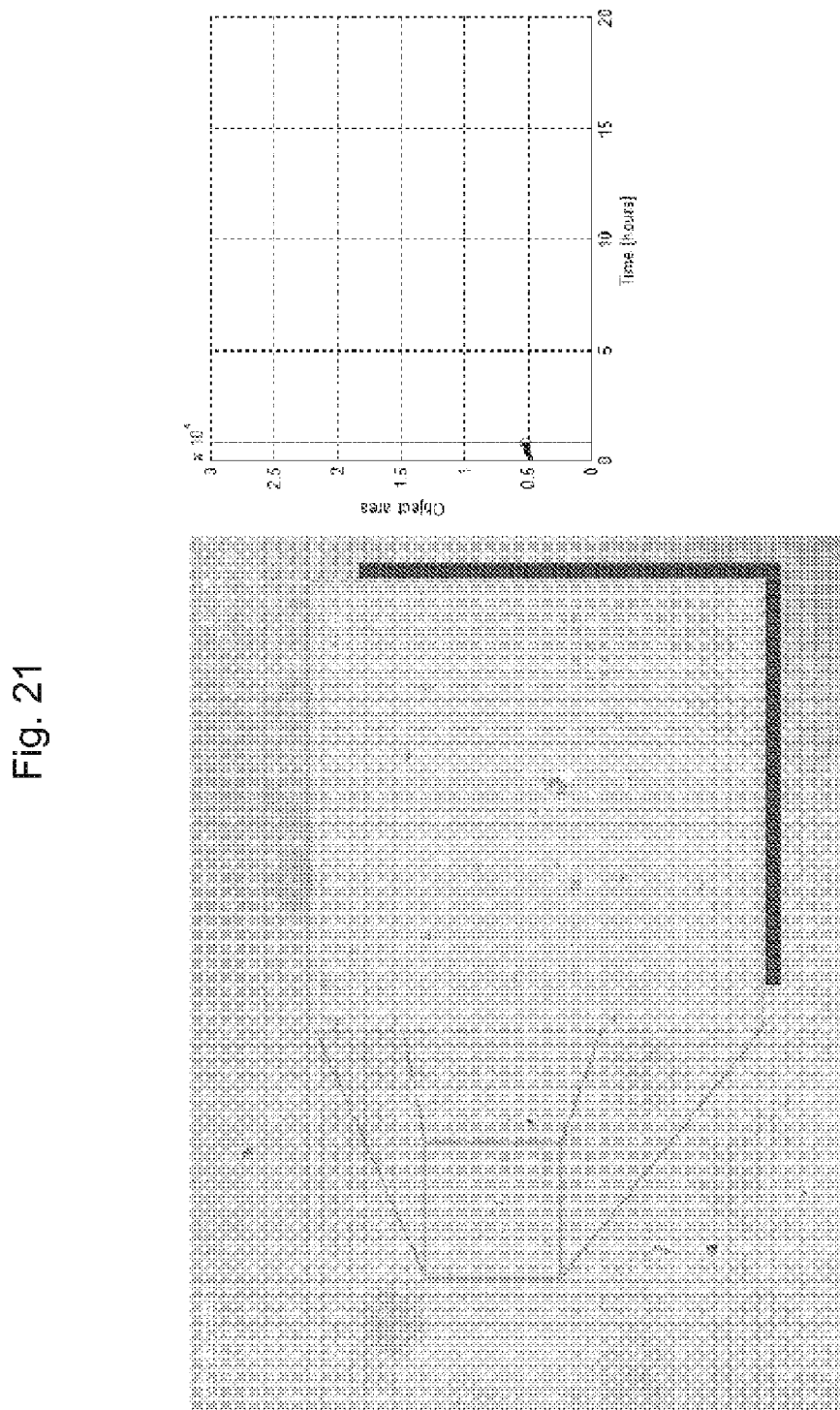
FIG. 21 shows a sample comprising *Acidophilus* bacteria just after preparation
Figure 22:
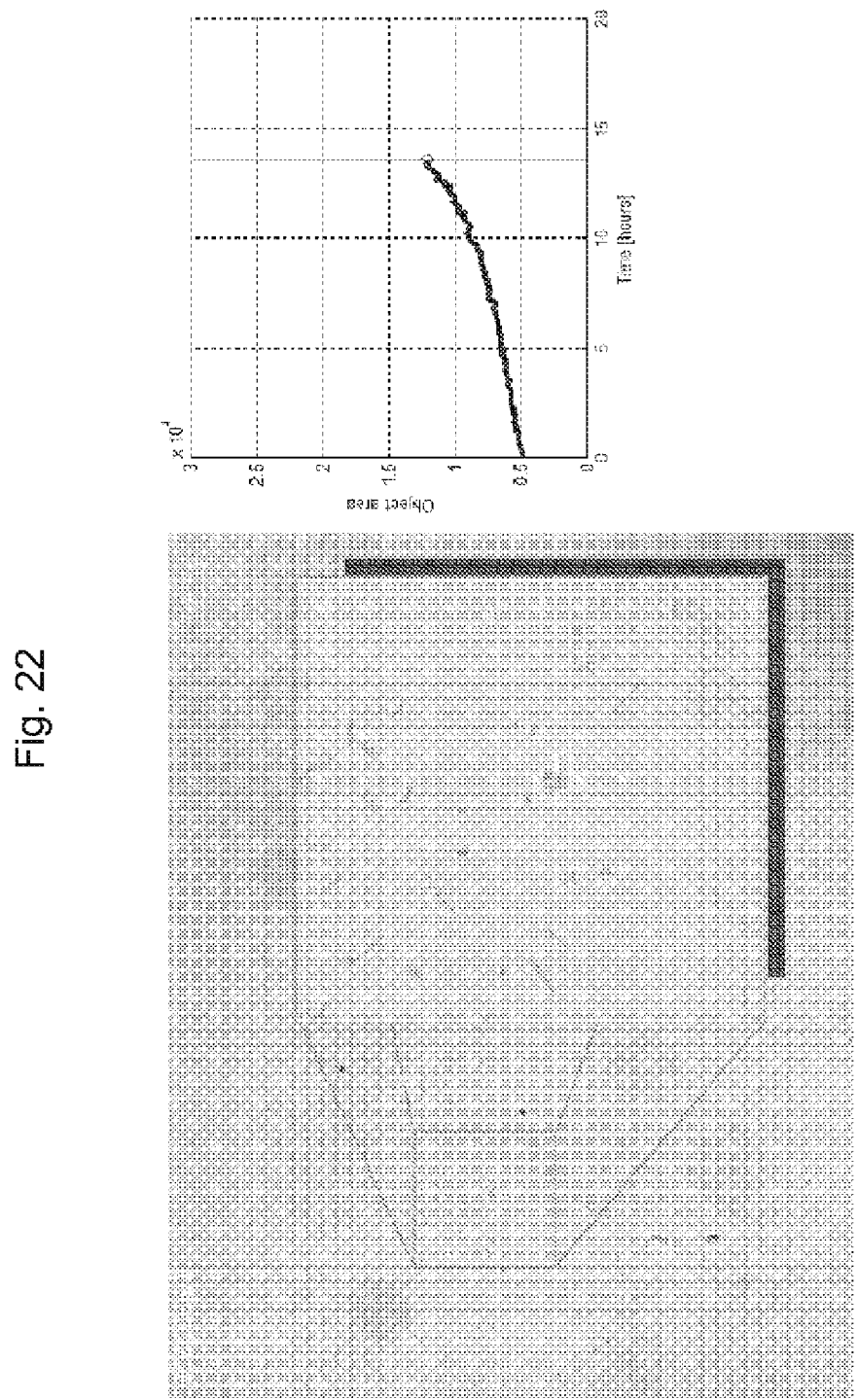
FIG. 22 shows the same sample as in FIG. 21, but after app. 13 hours
Figure 23:
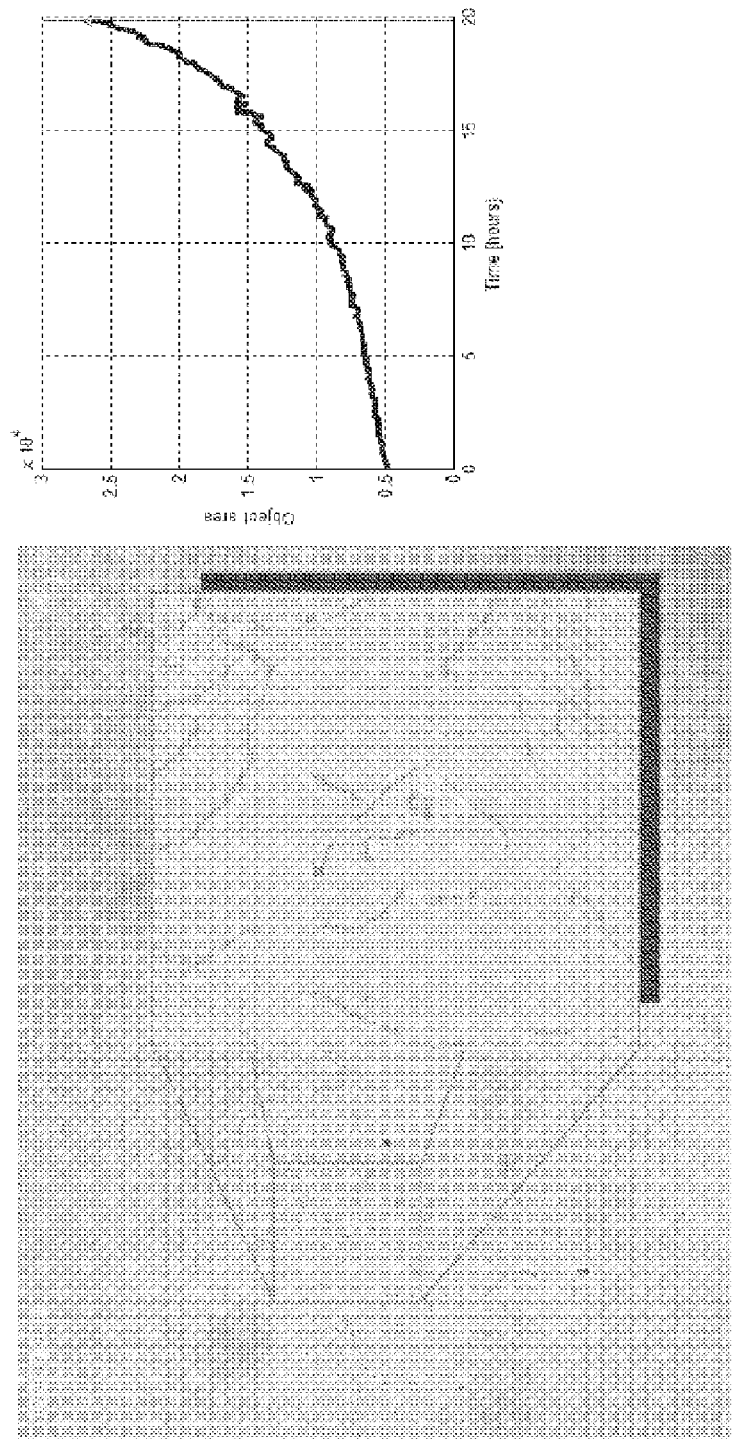
FIG. 23 shows the same sample as in FIG. 21, but after app. 20 hours The figures are schematic and may be simplified for clarity. Throughout, the same reference numerals are used for identical or corresponding parts.

FIG. 21-23 shows the development of a sample containing *Acidophilus* bacteria. The bacteria are initially placed in a sample containing a nutrition agent. The FIGS. 21-23 comprise each two subfigures. The leftmost subfigure is an image of the bacteria sample using bright field microscopy. A zoomed portion of the image is displayed on the top of the image to improve the visibility of the bacteria. The portion is indicated by the light rectangle. The rightmost subfigure shows the amount of bacteria mass as a function of time, i.e. a growth curve. The amount of bacteria mass is calculated as the total image area occupied by bacteria. FIG. 21 shows the sample just after preparation. Note the small circular bacteria. FIG. 22 shows the same sample after approximately 13 hours. Note how the bacteria changes shape due to rapid growth. FIG. 23 shows the sample after 20 hours. Notice the growth curve—this is an example of exponential growth.

The invention claimed is:

1. A system for determination of a value for at least one parameter describing microbial activity of individual biological organisms in a liquid sample comprising a plurality of biological organisms, said system comprising:
    an option detection assembly comprising at least one image acquisition device adapted to acquire images wherein individual biological organisms may be identified,
    at least one sample device comprising at least one sample container for holding the sample in liquid form,
    at least one translating unit arranged to move said liquid sample device and said optical detection assembly relative to each other,
    a control unit for controlling said optical detection assembly and said translating unit, said control unit is adapted to sequentially acquire optical sectionings from said liquid sample comprising at least a first and a second optical sectioning of the same biological organisms in said liquid sample, each of the optical sectionings comprises several images of the plurality of biological organisms, and there being a first time interval between acquisitions of said at least first and second optical sectioning,
    an image analysing device for analysing said images of said first and said second optical sectionings wherein said image analysing device comprises algorithms adapted to determine said value for said at least one parameter describing microbial activity of said individual biological organisms in each sample container.

2. The system according to claim 1, wherein said optical detection assembly further comprises an image illumination device.

3. The system according to claim 2, wherein said image illumination device comprises a light source selected from a laser, a diode laser, a LED, a light bulb, a white light source or a polarized light source.

4. The system according to claim 1 further comprising a stimulating device for providing stimulation to said sample in said sample device.

5. The system according to claim 4, wherein said stimulation comprises applying an electromagnetic field, a magnetic field, an electric field or an acoustic wave.

6. The system according to claim 1, further comprising a liquid sample environment controlling device adapted to control at least one of a physical environment of said biological organisms in said liquid sample, and a chemical environment of said liquid sample.

7. The system according to claim 6, wherein said liquid sample environment controlling device is adapted to control temperature of said liquid sample.

8. The system according to claim 6, wherein said liquid sample environment controlling device is adapted to control at least pH value, level of nutrition, partial pressure of gasses, salinity, level of alkali metal ions or level of alkaline earth metals.

9. The system according to claim 1, wherein said parameter is selected from a group of cell division rate, cell viability, living/dead rate, Brownian movements, metabolic rate, morphology, growth factor, kinetics and focus behaviour.

10. The system according to claim 1, wherein said microbial activity comprises the microbial susceptibility of said biological organisms toward an antibiotic agent.

11. The system according to claim 1, wherein the number of sample containers $N_{cont}$ on sample device equals 2, 3, 4, 5, 6, 8, 9, 10, 12, 14, 15, 16, 18, 20, 21, 22, 24, 25, 26, 27, 28, 30, or more than 30.

12. The system according to claim 1, wherein at least a part of said sample containers are inoculated with a first agent.

13. The system according to claim 12, wherein at least a part of said sample containers are inoculated with $N_{agent}$ different agents, where $N_{agent}$ is 2, 3, 4, 5, 6, 8, 10, 20, or more than 20.

14. The system according to claim 1, wherein said control unit is adapted to acquire optical sectionings from each sample container over a period of time.

15. The system according to claim 14, wherein said period of time is below 144 hours.

16. The system according to claim 14, wherein said period of time is below 2700 seconds.

17. The system according to claim 14, wherein said control unit is adapted to change said period of time depending on said determined value of said parameter.

18. The system according to claim 1, wherein said control unit is adapted to sequentially acquire optical sectionings from at least two different sample containers with a first time interval between the acquisition of following two optical sectionings.

19. The system according to claim 1, wherein said control unit is adapted to sequentially acquire optical sectionings from a sample container with a second time interval between two subsequent sectionings from a sample container.

20. The system according to claim 18, wherein said control unit is adapted to change said first time interval depending on said determined value of said parameter.

21. The system according to claim 19, wherein said f control unit is adapted to change said second time interval depending on said determined value of said parameter.

22. The system according to claim 1, wherein said control unit is adapted to stop image acquisition when said value of said parameter satisfies a predetermined condition.

23. The system according to claim 22, wherein said predetermined condition is related to the determination of antibiotic susceptibility of said biological organisms or to the determination of minimum inhibitory concentration (MIT).

24. A method for determining of microbial activity in a liquid sample comprising a plurality of biological organisms, said method comprising
   sequentially acquiring a plurality of optical sectionings of said liquid sample that comprises a plurality of biological organisms, each of the optical sectionings comprises several images of the same plurality of biological organisms, and each optical sectioning is taken at a different point in time,
   selecting a first and a second optical sectioning from said plurality of sectionings, there being a first time interval between the acquisitions of said at least first and section optical sectioning,
   computing a value of at least one parameter for each optical sectioning,
   determining if a change in said value of said at least one parameter has occurred between said first and second optical sectionings, and
   determining said microbial activity in said liquid sample from said change in said value of said at least one parameter.

25. The method according to claim 24, wherein said microbial activity is related to biological organisms selected from bacteria, archaea, yeast, fungi, pollen, viruses, leukocytes, such as granulocytes, monocytes, Erythrocytes, Thrombocytes, oocytes, sperm, zygote, or stem cells.

26. The method according to claim 24, wherein said microbial activity is related to biological organisms comprised in clinical material selected from faeces, swap samples from skin, lesions, serosal or mucosal surfaces, urine, lymph, pus, expectorate, transudate, exudates, glandular excretions such as milk, sweat, saliva, tear fluid, sebaceous discharge, nasal or other mucosal discharge, blood, cerebrospinal fluid, timorous tissue, biopsies material from any tissue, extracellular fluid, serum or plasma.

27. The method according to claim 24, wherein said liquid sample is comprised in at least one sample container.

28. The method according to claim 27, wherein optical sectionings are acquired from two different sample containers, and wherein said sequence of acquiring said optical sectioning comprises waiting a predetermined first time interval between acquiring two following optical sectionings.

29. The method according to claim 28, wherein said first interval is below about 1800 seconds.

30. The method according to claim 27, wherein said sequence of acquiring said optical sectioning comprise waiting a predetermined second time interval between acquiring optical sectionings from the same sample container.

31. The method according to claim 30, wherein said second interval is below about 3600 seconds.

32. The method according to claim 24, wherein optical sectionings from one sample container is acquired over a period of time.

33. The method according to claim 32, wherein said period of time is below about 72 hours.

34. The method according to claim 32, wherein said period of time is below about 2700 seconds.

35. The method according to claim 24, further applying an external stimulation to said liquid sample.

36. The method according to claim 35, wherein said stimulation comprises applying a magnetic field, an electrical field, an electromagnetic field or an acoustic wave.

37. The method according to claim 27, wherein said at least one sample container is inoculated with at least a first agent before said liquid sample is introduced into said sample container or while said liquid sample is in said sample container.

38. The method according to claim 37, wherein at least a part of said sample containers are inoculated with $N_{agent}$ different agents, where $N_{agent}$ is at least 2.

39. The method according to claim 37, wherein at least one sample container is substantially free of an agent.

40. The method according to claim 37, wherein said agent(s) is/are selected from antibiotics, nutrients, disinfectant, cleaning detergents, or combinations thereof.

41. The method according to claim 37, wherein said agent(s) is/are inoculated in different concentrations in at least two sample containers.

42. The method according to claim 24, wherein at least one of chemical environment of said biological organisms in said liquid sample and physical environment of said biological organisms in said liquid sample is controlled.

* * * * *